(12) United States Patent
Romanovsky et al.

(10) Patent No.: US 10,488,348 B2
(45) Date of Patent: Nov. 26, 2019

(54) WAFER INSPECTION

(71) Applicant: KLA-Tencor Corporation, Milpitas, CA (US)

(72) Inventors: Anatoly Romanovsky, Palo Alto, CA (US); Ivan Maleev, Pleasanton, CA (US); Daniel Kavaldjiev, San Jose, CA (US); Yury Yuditsky, Mountain View, CA (US); Dirk Woll, San Jose, CA (US); Stephen Biellak, Sunnyvale, CA (US); Mehdi Vaez-Iravani, Los Gatos, CA (US); Guoheng Zhao, Palo Alto, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/882,946

(22) Filed: Jan. 29, 2018

(65) Prior Publication Data

US 2018/0164228 A1 Jun. 14, 2018

Related U.S. Application Data

(63) Continuation of application No. 14/838,194, filed on Aug. 27, 2015, now Pat. No. 9,915,622, which is a
(Continued)

(51) Int. Cl.
*G01N 21/95* (2006.01)
*G01N 21/88* (2006.01)
(Continued)

(52) U.S. Cl.
CPC ......... *G01N 21/9501* (2013.01); *G01N 21/47* (2013.01); *G01N 21/8806* (2013.01); *G01N 21/8851* (2013.01); *G01N 21/956* (2013.01)

(58) Field of Classification Search
CPC ............... G01N 21/9501; G01N 21/47; G01N 21/8806; G01N 21/8851; G01N 21/956
(Continued)

(56) References Cited

U.S. PATENT DOCUMENTS

| 5,929,986 A | 7/1999 | Slater et al. |
| 6,208,411 B1 | 3/2001 | Vaez-Iravani |

(Continued)

FOREIGN PATENT DOCUMENTS

| JP | 2002-508513 | 3/2002 |
| JP | 2002-544477 | 12/2002 |

(Continued)

*Primary Examiner* — Isiaka O Akanbi
(74) *Attorney, Agent, or Firm* — Ann Marie Mewherter

(57) ABSTRACT

Systems configured to inspect a wafer are provided. One system includes an illumination subsystem configured to direct pulses of light to an area on a wafer; a scanning subsystem configured to scan the pulses of light across the wafer; a collection subsystem configured to image pulses of light scattered from the area on the wafer to a sensor, wherein the sensor is configured to integrate a number of the pulses of scattered light that is fewer than a number of the pulses of scattered light that can be imaged on the entire area of the sensor, and wherein the sensor is configured to generate output responsive to the integrated pulses of scattered light; and a computer subsystem configured to detect defects on the wafer using the output generated by the sensor.

57 Claims, 9 Drawing Sheets

Related U.S. Application Data continuation of application No. 13/544,954, filed on Jul. 9, 2012, now Pat. No. 9,279,774.

(60) Provisional application No. 61/506,892, filed on Jul. 12, 2011.

(51) Int. Cl.
*G01N 21/47* (2006.01)
*G01N 21/956* (2006.01)

(58) Field of Classification Search
USPC .......................................... 356/237.2–237.6
See application file for complete search history.

(56) References Cited

U.S. PATENT DOCUMENTS

| | | | |
|---|---|---|---|
| 8,194,301 | B2 | 6/2012 | Zhao et al. |
| 2004/0042001 | A1 | 3/2004 | Vaez-Iravani et al. |
| 2005/0018182 | A1* | 1/2005 | Hyun ................. G01N 21/9501 356/237.4 |
| 2008/0068593 | A1* | 3/2008 | Nakano ............ G01N 21/95607 356/73 |
| 2008/0165343 | A1 | 7/2008 | Lewis et al. |
| 2009/0040511 | A1 | 2/2009 | Wolters et al. |
| 2009/0225399 | A1 | 9/2009 | Zhao et al. |
| 2009/0323052 | A1 | 12/2009 | Silberstein et al. |
| 2010/0004875 | A1* | 1/2010 | Urano ................ G01N 21/4738 702/40 |
| 2010/0188657 | A1 | 7/2010 | Chen et al. |
| 2012/0092484 | A1* | 4/2012 | Taniguchi .......... G01N 21/9501 348/87 |
| 2012/0133928 | A1* | 5/2012 | Urano ................ G01N 21/9501 356/237.2 |

FOREIGN PATENT DOCUMENTS

| | | |
|---|---|---|
| JP | 2005-524827 | 8/2005 |
| JP | 2007-086100 | 4/2007 |
| JP | 2009-501902 | 1/2009 |
| JP | 2010-256148 | 11/2010 |
| WO | 2000/068673 | 11/2000 |
| WO | 2010/085679 | 7/2010 |

\* cited by examiner

WAFER INSPECTION

BACKGROUND OF THE INVENTION

1. Field of the Invention

This invention generally relates to systems configured to inspect a wafer.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Improved sensitivity to particles, anomalies, and other defect types, while maintaining overall inspection speed (in wafers per hour), is desired in wafer inspection systems. Dark field optical inspection systems typically use laser light to illuminate the wafer in a specific pattern—individual spots, lines, or areas—and collection optics to direct the scattered light on a corresponding set of sensors.

One advantage of an inspection system where a large area (on the order of 1 mm by 1 mm) of the wafer is illuminated at once, as opposed to a spot (on the order of microns) or a line (on the order of microns wide by mm long), is that there exist many varieties of two-dimensional sensors that can capture information on thousands to millions of individual detectors in parallel. Furthermore, spot-illuminated inspection systems are practically limited to dozens of spots due to the complexities of illumination optics and of integrating individual sensors thereby limiting achievable throughput. One further disadvantage of spot and line scanning systems is the illumination energy is concentrated. In relatively small areas, increasing the power density on the inspected surface, which can undesirably alter the sample properties.

It is well known that an XY (or serpentine) inspection sequence offers lower inspection throughput than a spiral sequence; therefore, a spiral trajectory (commonly known as R-Theta) is desirable under some circumstances. Examples of spiral inspection systems include the SP1 and SP2 instruments, commercially available from KLA-Tencor Corporation, Milpitas, Calif.

Despite the advantage of area inspection systems, as described above and in the art (e.g., U.S. Pat. No. 7,286,697 to Guetta), implementation of this configuration on an R-Theta platform has proven challenging, as there is an inherent mismatch of the spiral sequence of generated images with the rectilinear nature of most two-dimensional array sensors. Detection of defects by the aligning and registration of polar images in real time is a computationally intensive activity. Furthermore, the additional noise added to the measurement by most two-dimensional silicon-based sensors, as compared to discrete detectors such as photo-multiplier tubes (PMTS), has in practice reduced the sensitivity performance of such systems. On XY-based area inspection systems, the coordinate mismatch problem does not exist, but previous embodiments of such systems have not been able detect all defects of interest at high speeds due to lack of flexibility of the illumination and collection subsystems.

Accordingly, it would be advantageous to develop inspection systems and/or methods that do not have one or more of the disadvantages described above.

SUMMARY OF THE INVENTION

The following description of various embodiments is not to be construed in any way as limiting the subject matter of the appended claims.

One embodiment relates to a system configured to inspect a wafer. The system includes an illumination subsystem configured to simultaneously form multiple illumination areas on the wafer with substantially no illumination flux between each of the areas. The system also includes a scanning subsystem configured to scan the multiple illumination areas across the wafer. In addition, the system includes a collection subsystem configured to simultaneously and separately image light scattered from each of the areas onto two or more sensors. Characteristics of the two or more sensors are selected such that the scattered light is not imaged into gaps between the two or more sensors. The two or more sensors generate output responsive to the scattered light. The system further includes a computer subsystem configured to detect defects on the wafer using the output of the two or more sensors. This system may be further configured as described herein.

Another embodiment relates to another system configured to inspect a wafer. This system includes an illumination subsystem configured to direct multiple light beams to substantially the same area on a wafer. The multiple light beams have substantially the same wavelength and polarization characteristics. The system also includes a scanning subsystem configured to scan the multiple light beams across the wafer. In addition, the system includes a collection subsystem configured to image light scattered from the substantially the same area on the wafer to a sensor. The sensor generates output responsive to the scattered light. The system further includes a computer subsystem configured to detect defects on the wafer using the output of the sensor. This system may be further configured as described herein.

An additional embodiment relates to a system configured to inspect a wafer. This system includes an illumination subsystem configured to direct a first of multiple pulsed light beams to an area on a wafer earlier in time than a second of the multiple pulsed light beams is directed to the area by the illumination subsystem. The first and second of the multiple pulsed light beams have different shapes and sizes on the wafer from each other. The first and second of the multiple pulsed light beams have different wavelengths from each other, different polarizations from each other, or different wavelengths and polarizations from each other. The system also includes a scanning subsystem configured to scan the multiple pulsed light beams across the wafer. In addition, the system includes a collection subsystem configured to image light scattered from the area on the wafer to one or more sensors. The one or more sensors generate output responsive to the scattered light. The system further includes a computer subsystem configured to detect defects on the wafer using the output of the one or more sensors and to use the output responsive to the scattered light from the area due to illumination by the first of the multiple pulsed light beams to determine a power of the second of the multiple pulsed light beams that should be directed to the area. This system may be further configured as described herein.

A further embodiment relates to another system configured to inspect a wafer. This system includes an illumination subsystem configured to direct pulses of light to an area on a wafer. The system also includes a scanning subsystem configured to scan the pulses of light across the wafer. In addition, the system includes a collection subsystem configured to image pulses of light scattered from the area on the wafer to a sensor. The sensor is configured to integrate a number of the pulses of scattered light that is fewer than a number of the pulses of scattered light that can be imaged on the entire area of the sensor. The sensor is configured to generate output responsive to the integrated pulses of scattered light. The system further includes a computer subsystem configured to detect defects on the wafer using the output generated by the sensor. This system may be further configured as described herein.

Another embodiment relates to a system configured to inspect a wafer. This system includes an illumination subsystem configured to direct light to an area on a wafer. The system also includes a scanning subsystem configured to scan the light across the wafer. In addition, the system includes a collection subsystem configured to image light scattered from the area on the wafer to a sensor. The sensor is configured to generate output responsive to the scattered light. The system further includes a computer subsystem configured to detect point defects on the wafer using the output generated by the sensor, to determine a size, in pixels, of the point defects, to determine a focal condition of the system based on the size of the point defects, and to alter one or more parameters of the system based on the focal condition. This system may be further configured as described herein.

An additional embodiment relates to a system configured to inspect a wafer. The system includes an illumination subsystem configured to direct light to an area on a wafer. The system also includes a scanning subsystem configured to scan the light across the wafer. In addition, the system includes a collection subsystem configured to image light scattered from the area on the wafer to a sensor. The sensor is configured to generate output responsive to the scattered light. The system also includes a computer subsystem configured to detect defects on the wafer using the output generated by the sensor. This system may be further configured as described herein.

BRIEF DESCRIPTION OF THE DRAWINGS

Other objects and advantages of the invention will become apparent upon reading the following detailed description and upon reference to the accompanying drawings in which.

Figure 1:
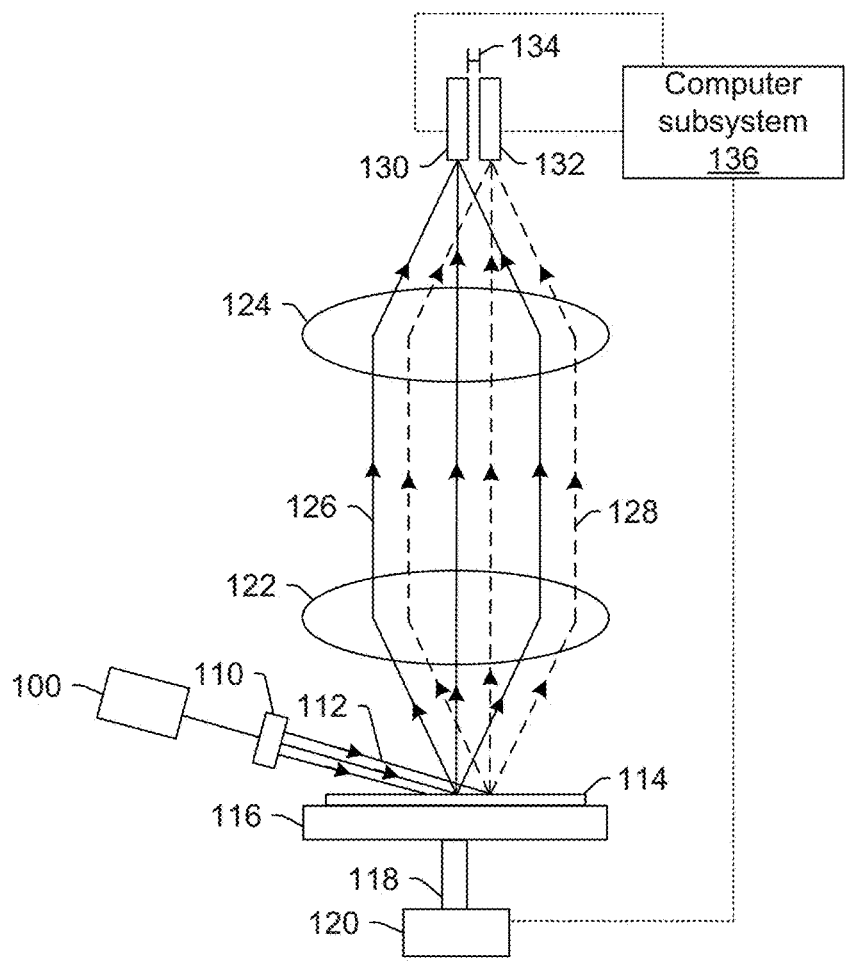
FIG. 1 is a schematic diagram illustrating a side view of one embodiment of a system configured to inspect a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

In general, the embodiments described herein relate to wafer inspection methods and systems that include the following: illumination (e.g., laser illumination) is incident on the wafer; the wafer or illumination spot(s) on the wafer is/are translated in some fashion; scattered light is collected by a collection subsystem (which may include a collection objective); in the collection optics, the scattered light may be divided based on selectable polarization and/or scattering angle characteristics; selected portion(s) of the scattered light are directed onto one or more sensors; and defects are detected by processing output (e.g., image information) generated by the sensor(s).

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a system configured to inspect a wafer. In order to optimize inspection speed and/or sensitivity, a spatially discontinuous illumination profile may be used. For example, this system includes an illumination subsystem configured to simultaneously form multiple illumination areas on the wafer with substantially no illumination flux between each of the areas. In this manner, the system is configured for multi-spot ("multi-patch") area inspection.

All of the illumination subsystems described herein include one or more light sources possibly coupled to some illumination optics. For example, multi-patch illumination can be generated by 3 methods: multiple lasers with one patch per laser; multiple laser beams from one laser; and a diffractive optical element separating the beams of one or more lasers. In one such example, the illumination subsystem may include a laser source (or sources) illuminating the wafer with polarized light at a specific angle of incidence or multiple discrete angles of incidence. The optimal illumination angle(s) of incidence for inspection depend on the wafer type being inspected and the defects of interest to be detected among other factors. The illumination subsystem may be configured to allow for illumination at near normal incidence and/or an oblique angle of 45 degrees or greater, either sequentially or simultaneously. In addition, the laser source may be a pulsed laser.

The multiple illumination areas may have different cross-sectional shapes on the wafer such as substantially flat-top, Gaussian, non-Gaussian, any other structured area illumination, etc. For example, multiple flat-top illumination areas may be formed on the wafer, with no illumination flux in between these areas. The multiple illumination areas may be formed on a surface of the wafer such as an uppermost surface of the wafer. However, the multiple illumination areas may be formed on a wafer with films, at a particular interface in a film stack, or even subsurface (e.g., within the wafer).

Figure 2:
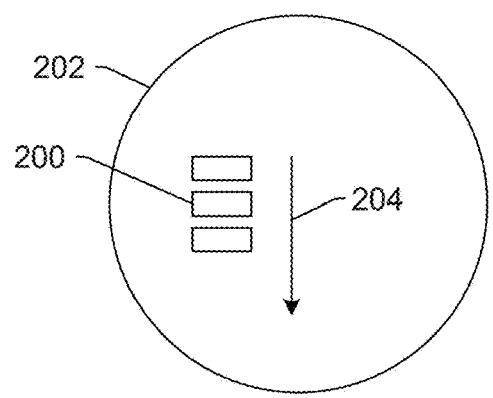
FIG. 2 is a schematic diagram illustrating a plan view of one embodiment of multiple illumination areas having a rectangular shape on a wafer.

In one embodiment, each of the multiple illumination areas has a rectangular shape on the wafer. For example, as shown in FIG. 2, each of multiple illumination areas 200 may have a rectangular shape on wafer 202, and the direction of wafer travel may be in the direction shown by arrow 204. In the embodiment shown in FIG. 2, three separate illumination areas (or patches) are formed on the wafer as described further herein (e.g., either by three separate laser beams or a diffractive optical element). Interleaving of the patches may be accomplished in a similar fashion to that used in current multi-spot inspection systems.

One advantage of this implementation in laser area inspection is that it is a solution to the problem that relatively fast sensors tend to be substantially rectangular (i.e., one dimension of the sensor is substantially longer than the other dimension). It is difficult to make a substantially rectangular (e.g., 40:1 or 100:1 aspect ratio) patch on a wafer. In the implementations described herein, three 13:1 or 33:1 aspect ratio patches could take the place of one 40:1 or 100:1 patch, respectively, and three slower sensors can take the place of one larger, substantially elongated sensor. In general, for area inspection mode systems, ratios between 1:1 and 100:1 can be considered. In an embodiment, the multiple illumination areas do not overlap with each other on the wafer. For example, since this system is "flash on the fly," the patches can be arranged so they do not overlap on the wafer, and the stage (described further herein) will move just the correct amount between each flash. The patches can also be projected as a 1×3 array instead of a 3×1 array if more convenient. "A rectangular shape on the wafer" as that term is used herein generally refers to a shape that is substantially rectangular but may not be exactly rectangular due to, for example, the inherent limitations of imaging any light beam.

In one embodiment, the illumination subsystem forms the multiple illumination areas on the wafer using multiple light beams generated from a single light beam. For example, the multiple light beams may be generated from one beam using a diffractive optical element. In one such embodiment shown in FIG. 1, the illumination subsystem includes light source 100 and diffractive optical element 110. The light source and the diffractive optical element are configured such that a light beam generated by the light source is directed to the diffractive optical element and the diffractive optical element generates two or more three) light beams 112 from that single light beam. The light source may include any of the light sources described herein, and the diffractive optical element may include any suitable diffractive optical element known in the art. As shown in FIG. 1, the multiple light beams may be directed to wafer 114 at an oblique angle of incidence. However, the multiple light beams may be directed to the wafer at any other suitable angle of incidence as described further herein. The illumination subsystem shown in FIG. 1 may include any other suitable optical element(s) such as reflective optical elements, refractive optical elements, polarizers, apertures, beam shaping elements, wavelength filters, and the like.

Figure 3:
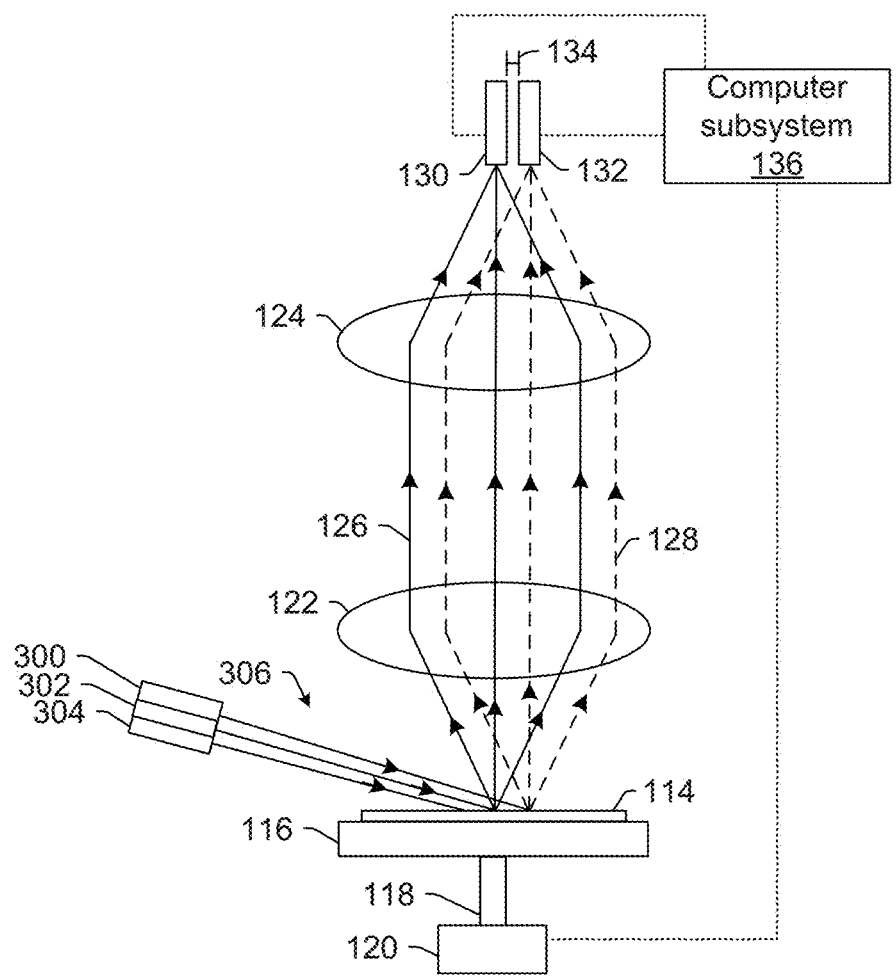
FIGS. 3-6 are schematic diagrams illustrating side views of various embodiments of a system configured to inspect a wafer.

In another embodiment, the illumination subsystem forms the multiple illumination areas on the wafer using multiple light beams generated by multiple light sources. For example, as shown in FIG. 3, the illumination subsystem may include multiple light sources 300, 302, and 304. The light sources may include any of the light sources described herein such as pulsed lasers. Each of the multiple light sources is configured to generate light having the same characteristics (e,g., each of the multiple light sources may be the same make and model laser). As shown in FIG. 3, the multiple light sources may generate multiple light beams 306, and the multiple light beams may be directed to wafer 114 at the same angle of incidence or roughly the same angle of incidence. However, the multiple light beams may be three laser beams injected at different angles. In addition, although the multiple light beams are shown in FIG. 3 as being directed to the wafer at an oblique angle of incidence, the multiple light beams may be directed to the wafer at a normal or near normal angle of incidence. The illumination subsystem shown in FIG. 3 may include any other suitable optical element(s) such as those described above. The system shown in FIG. 3 may be further configured as described herein.

Figure 6:
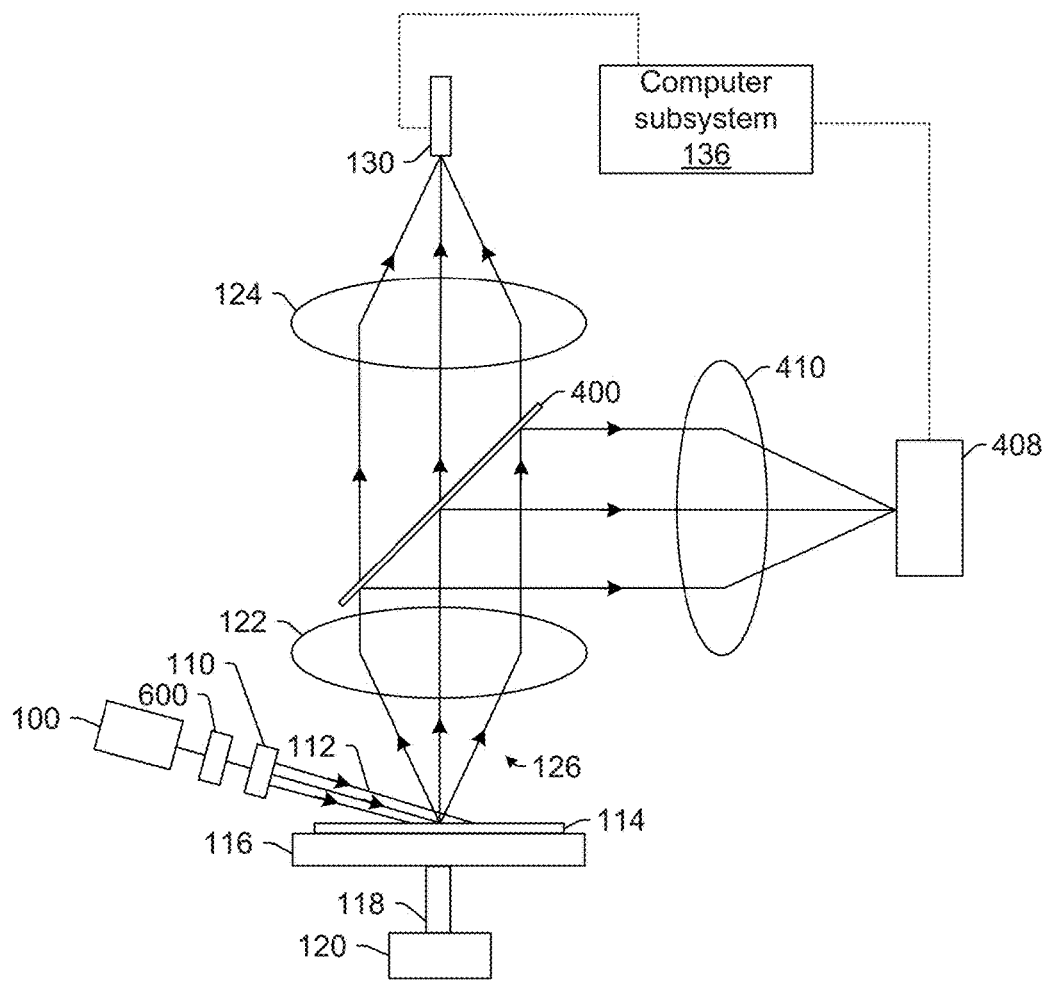

In some embodiments, the illumination subsystem includes a frequency conversion laser, the illumination subsystem is configured to simultaneously form the multiple illumination areas using pulses of light, and the pulses of tight directed to the areas on the wafer do not vary spatially over the duration of the pulses of light and have substantially constant intensity over the duration of the pulses of light. For example, the illumination subsystems described herein may use a frequency conversion laser with spatial flat-top illumination and temporal flat-top illumination output, in area mode inspection. Area-mode inspection systems often utilize Gaussian or "flat top" illumination profiles that are continuous on the surface of the wafer. In one such embodiment, the illumination subsystem includes a beam shaping optical element coupled to the laser. For example, as shown in FIG. 6, the illumination subsystem may include beam shaping optical element 600 coupled to light source 100, which in this instance may be a laser. The beam shaping optical element may include any suitable beam shaping optical element known in the art. In addition, although the beam shaping optical element is shown coupled to only one light source in FIG. 6 such that it is in the path of only one light beam, a beam shaping optical element may be coupled to each of the light sources included in any of the illumination subsystems described herein or may be positioned in the path of each of the illumination beams used by the systems described herein. The illumination subsystem and system shown in FIG. 6 may be further configured as described herein. The flat top beam may not only be generated by a diffractive optical element or other beam shaping optic external to the laser but also within the laser itself as a natural consequence of an optimized nonlinear frequency conversion process. One additional option is to utilize a laser that provides a user-specified temporal pulse shape, in order to further reduce the wafer damage probability. For instance, most common pulsed lasers exhibit an approximately hyperbolic secant pulse shape in time with a peak intensity more than 2× the average intensity. However, recent developments in laser technology have permitted so-called "flat-top" or "box car" temporal pulse shapes to be generated. The peak intensity of these pulses is essentially the same as the average intensity, and an improvement of ~2× may be achieved in inspection throughput.

In another embodiment, the illumination subsystem includes a frequency conversion laser, the illumination subsystem is configured to simultaneously form the multiple illumination areas using pulses of light, and the pulses of light directed to the areas on the wafer have substantially constant intensity over the duration of the pulses of light. Such an embodiment may be configured as described above except that the pulses of light are allowed to vary spatially over the duration of the pulses of light.

The system also includes a scanning subsystem configured to scan the multiple illumination areas across the wafer. The scanning subsystem may include a chuck that holds the wafer in place during inspection. For example, as shown in FIG. 1, the scanning subsystem may include chuck 116. The chuck could be an edge grip chuck, a vacuum chuck, or an air bearing check. One chuck may support multiple wafer diameters (e.g., 300 mm and 450 mm, for example) or a single substrate diameter. The scanning subsystem may also include shaft 118 coupled to chuck 116 and coupled to positioning subsystem 120. The positioning subsystem may include various elements such as a motor, gears, stages, and the like that are configured to rotate and/or translate shaft 118. Shaft 118 may be coupled to chuck 116 in such a manner that rotation and/or translation of the shaft causes rotation and/or translation of the chuck and thereby the wafer.

The scanning subsystem may translate the wafer, either in a spiral or X-Y fashion, or as described further herein some combination of the two. In particular, in addition to a spiral scan as described above, both X-Y serpentine scans and RT-XY hybrid scans may be employed to translate the wafer relative to the illumination and collection optics. A spiral motion inspection system as described herein is analogous to the SP1 and SP2 inspection systems that are commercially available from KLA-Tencor, Milpitas, Calif. with some notable exceptions described herein. For example, the illumination area(s) on the wafer are substantially large, typically extending for hundreds of microns up to several millimeters, the spindle rotation rate is relatively modest, typically not exceeding 1,000 to 5,000 rpm, and the collection subsystem may have near diffraction-limited performance. Furthermore, substrates up to and beyond 450 mm in diameter are inspectable by the systems described herein.

Figure 7:
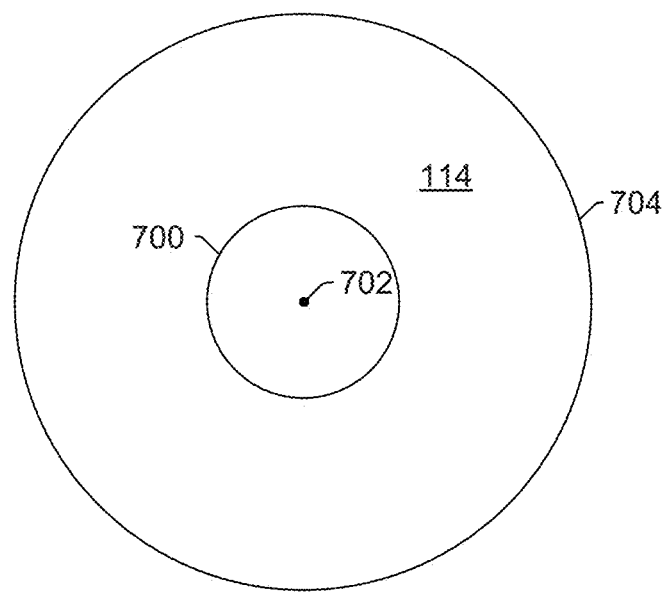
FIG. 7 is a schematic diagram illustrating a plan view of one embodiment of a center region of a wafer and a region outside of the center region of the wafer.

In a spiral inspection system, the rotation rate at the center of the wafer should be sufficient to support the generation of inspection frames with the desired overlap. In one embodiment, the illumination subsystem is configured to simultaneously form the multiple illumination areas using pulses of light, the light scattered from each of the areas includes pukes of scattered light, the scanning subsystem is configured to scan the pulses of light across the wafer by rotating the wafer, and when the pulses of light are being scanned across a center region of the wafer, the illumination subsystem is configured to simultaneously direct the pulses of light to the multiple illumination areas on the wafer less often than when the pulses of tight are being scanned across the wafer outside of the center region. For example, for inspection using a pulsed laser and an area sensor on a rotary stage, near the center of the wafer as the linear velocity of the wafer decreases at the center of the wafer proportional to the radius, the laser pulse may be triggered less and less often. In this manner, the scan proceeds at a slower rate in area per time while the sensitivity of inspection remains constant. The full average power of the laser is not utilized. Alternatively, the illuminated area can be reduced continuously during the scan as long as damage of the wafer is not induced by the light source. In one such embodiment shown in FIG. 7, center region 700 of wafer 114 may be a region encompassing center 702 of the wafer and spaced from edge 704 of the wafer. The center region may encompass the inner third of the wafer or the inner quarter of the wafer, for example. The portion of the wafer that is included in the center region of the wafer may vary depending on, for example, the speed of rotation of the wafer, the diameter of the wafer, the power of the laser, and any other parameters related to the power to which the wafer is exposed at any given time.

Figure 8:
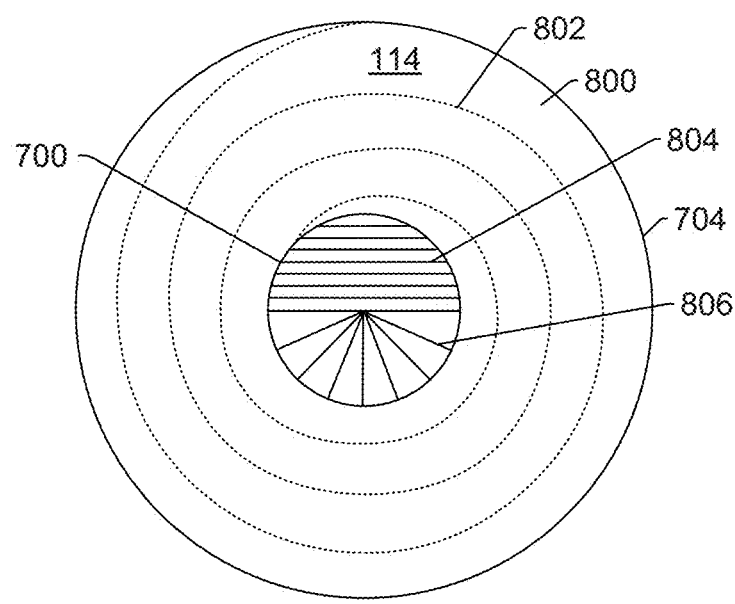
FIG. 8 is a schematic diagram illustrating a plan view of one embodiment of different manners in which a center region of a wafer and a region outside of the center region of the wafer may be scanned by the embodiments described herein.

In an embodiment, the illumination subsystem is configured to simultaneously form the multiple illumination areas using pulses of light, the light scattered from each of the areas includes pulses of scattered light, the scanning subsystem is configured to scan the pulses of light across the wafer by rotating and translating the wafer, the two or more sensors includes area sensors, when the pulses of light are being scanned across a center region of the wafer, the scanning subsystem scans the pulses of light across the wafer in one or more non-curved lines, and when the pulses of light are being scanned across the wafer outside of the center region, the scanning subsystem scans the pulses of light across the wafer in a spiral fashion. In this manner, the embodiments described herein may be configured for hybrid scanning during inspection with a pulsed laser and an area sensor on a rotary stage. For example, in the hybrid approach, most of the wafer may be scanned in a spiral fashion. In one such example as shown in FIG. 8, region 800 of wafer 114 outside of center region 700 of the wafer, which may be defined as described above, may be scanned in spiral fashion 802. Then, center region 700 of the wafer may be scanned with a series of small xy serpentine moves, or a single linear motion, or a combination of angular rotations followed by linear motions. In this manner, the center region may be scanned in linear fashion 804, in which the scans are performed in the x or y direction with step-wise translations in the opposite direction between scans, or in radial fashion 806, in Which the scans are performed along a radius of the wafer between step-wise rotations of the wafer. In this way, not inspecting any part of the wafer in the center of the wafer is avoided (which can happen if the alignment of the wafer relative to the scanning subsystem or optics is imperfect), properly aligning the output from the sensor(s) becomes less challenging, and the inspection throughput could increase. Furthermore, the effect of the "smearing" of the circular tracks across the rectangular sensor can be minimized, depending on the repetition rate of the source.

The system includes a collection subsystem configured to simultaneously and separately image light scattered from each of the areas onto two or more sensors. In general, the collection subsystems described herein may include some sort of scattered light collector (e.g., a collection objective such as scattered light collector 122 shown in FIG. 1) and possibly some additional optical elements coupled to the scattered light collector aperture(s), splitter(s), polarizing element(s), one or more reflective optical elements, and one or more refractive optical elements such as refractive optical element 124 shown in FIG. 1). The same collection lens may image the scattered light from each of the areas on a plurality of sensors. For example, as shown in FIG. 1, scattered light collector 122 may collect scattered light 126 from one of the multiple illumination areas on the wafer and scattered light 128 from another of the multiple illumination areas on the wafer.

The collection subsystem may include an objective lens or lenses to collect light scattered from the wafer. In addition to a relatively high numerical aperture (NA) objective, additional sets of lower NA, or even non-imaging, collection optics may be disposed in the collection hemisphere close to the horizon. Light scattering information from these angles will thereby be collected allowing further capture of defects and features of interest that would not be detected through the primary objective.

The collection subsystem may also include various elements to selectively filter the scattered light to enhance the capture rate of defects of interest and reduce the false alarm rate. The various elements may include elements such as the optical elements and micro-electro-mechanical system (MEMS)-based devices described herein. In addition, the various elements may include polarizers, beam splitters, apertures, spatial filters, and the like.

The collection subsystem may further include one or more optical elements configured to image the filtered light onto two or more sensors (e.g., two or more area sensors). For example, refractive optical element 124 shown in FIG. 1 may be configured to image the filtered light onto sensors 130 and 132 shown in FIG. 1.

In addition, the collection subsystem is preferably configured such that light from each of the multiple illumination areas on the wafer is separately imaged onto only a corresponding sensor. For example, as shown in FIG. 2, scattered light 126 from a first of the multiple illumination areas is only imaged onto sensor 130 while scattered light 128 from a second of the multiple illumination areas is only imaged onto sensor 132. In this manner, light from more than one of the multiple illumination areas will not be imaged onto the same sensor.

Characteristics of the two or more sensors are selected such that the scattered light is not imaged into gaps between the two or more sensors. For example, sensors 130 and 132 may be selected and configured such that scattered light 126 and 128 is not imaged into gap 134 between the two sensors. In one such example, two smaller, less expensive sensors may be utilized without experiencing an undesired loss of sensitivity from scattered laser light that would be otherwise imaged into the "gaps" between the sensors. Gaps between discrete sensors are often inevitable due to packaging constraints, supporting electronics, etc. In addition, with two-dimensional sensors and their inherent limitations (e.g., in their data rate, column rate, etc.), the light source(s) and the sensor(s) may not necessarily be coupled together very well. Some currently used systems include a focal plane array of sensors to overcome these limitations. However, in the embodiments described herein, the light source(s) and two-dimensional sensor characteristics are matched to overcome the limitations.

The two or more sensors generate output responsive to the scattered light. The two or more sensors may include point or relatively low resolution sensors. The two or more sensors may also include, for example, discrete photomultiptier tubes (PMTs), charge coupled devices (CCDs), time delay integrators (TDIs), complementary metal-oxide-semiconductor (CMOS) sensors, scientific CMOS's (sCMOS's), PMT arrays, electron-bombarded CCDs (EB-CCDs), electron-multiplying CCDs (EM-CCDs), intensified photodiodes, or avalanche photodiode (APD) arrays. Each channel and/or sensor may be configured to respond to the illumination wavelength or additional wavelengths generated by wafer interactions, or some combination of the two, by using wavelength filtering techniques. This allows for more selective detection of some types of defects of interest. In addition, the sensor(s) used in the systems described herein may vary depending on the type of scanning used for inspection and/or the light sources included in the illumination subsystem. For example, in an XY scanning configuration, a higher repetition rate mode-locked laser can be used to illuminate the wafer to possibly avoid laser-induced wafer damage with sensor(s) configured to acquire data in TDI mode.

In some instances, elements of the collection subsystem may be selected based on one or more characteristics of the two or more sensors. For example, in some cases, the collection subsystem may include one or more tube lenses, and the anamorphic ratios of the one or more tube lenses may be selected based on the aspect ratios of the two or more sensors. In addition, if different sensor types are used for different channels of the system, different tube lenses may have different anamorphic magnification to assure that each sensor is measuring the same area on the wafer.

An objective lens included in the collection subsystem may be a relatively high NA lens diffraction-limited over the field of view. Alternatively, a non-diffraction limited objective can be employed. For example, in one embodiment, the collection subsystem includes a scattered light collector having a resolution that is not fully diffraction-limited. In particular, the collector design and manufacturing may be appropriately matched, for reduced cost, to the distorted point spread function produced by relevant, typically employed, apertures and polarizers in the collection channels. The specification for the resolution of the objective can be calculated by knowing in advance a target defect geometry and material (e.g., a silica sphere), and pupil or Fourier plane filter that optimizes the capture rate of that defect, given the substrate type. A reduction of the resolution requirements from fully diffraction-limited can result in significant cost savings for system users.

The systems described herein may also include an autofocus subsystem (not shown). The autofocus subsystem may ensure that the surface of the wafer is always in focus at the sensor(s) regardless of the movement of the wafer, light source, collection optics, and illumination optics. The autofocus subsystem may include a light source (which may or may not be the light source used for inspection), sensor(s), circuits, and logic for determining the position of the wafer image relative to the sensor(s) (e.g., two-dimensional sensors), and a feedback system for correcting any deviations noted during the inspection. The autofocus subsystem may be further configured as described herein.

The system further includes a computer subsystem configured to detect defects on the wafer using the output of the two or more sensors. In this manner, the computer subsystem provides a means to detect defects in signals or other output produced by the sensors. For example, the system shown in FIG. 1 may include computer subsystem 136 coupled to the two or more sensors such that the computer subsystem can receive the output produced by the two or more sensors. The computer subsystem may be configured to detect the defects on the wafer using the output and any suitable defect detection algorithm and/or method. For example, the computer subsystem may apply a defect detection threshold to the output and any output found to be above the defect detection threshold may be identified as a defect or a possible defect.

The computer subsystem may include any suitable computer system known in the art. For example, computer subsystem 136 may take various forms, including a personal computer system, mainframe computer system, workstation, image computer, parallel processor, or any other device known in the art. In general, the term "computer subsystem" may be broadly defined to encompass any device having one or more processors, which executes instructions from a memory medium.

With regards to the collection of scattered light, one improvement of the embodiments described herein over currently used systems is the selective and configurable collection of surface scatter to enhance the detection of particles and defects. Some previously used systems include rotating spatial filter systems in the collection optics to remove the effects of pattern scatter and enhance scatter from point particles and defects. In the embodiments described herein, the filtering may be fixed during the wafer scan at a particular orientation to the illumination angle while the wafer rotates underneath. The filter rejects certain solid angles of collection (containing undesirable scattered light from the background rather than from defects of interest) by using a combination of multiple polarizers arranged at selected angles and movable sections of material opaque to the scattered wavelength. The filtering is performed in the back Fourier plane of the objective lens so that the undesired background at each point in the illuminated field may be simultaneously eliminated.

Multiple area-type sensors may also be used in conjunction with the spatial filtering techniques described herein. For example, the systems may include a flexible collection system where a plurality of sensors are selectively configured to detect scattered light with multiple polarization states and/or solid angles of scatter. Each sensor may be disposed to collect scattered light that the other sensors, if present, do not collect. In addition, each sensor may be a multi-element sensor and may have different Characteristics. For example, one sensor may be an intensified EB-CCD sensor. Another sensor may include a standalone magnetic-focus image intensifier coupled to a CCD or CMOS chip with a relay lens. A third sensor may be a lower resolution standalone CCD chip. Additional sensors may also be present. The sensor type and size for each channel may be selected based on the scattered background characteristics expected in that channel as well as the defects of interest sensitivity requirement in that channel. When the point spread function projected onto a particular sensor is expected to be large due to the spatial filtering, a lower resolution is preferred. In this way, the system may be optimized with lower cost sensors in channels where other noise sources dominate in order to reduce operating costs.

Figure 4:
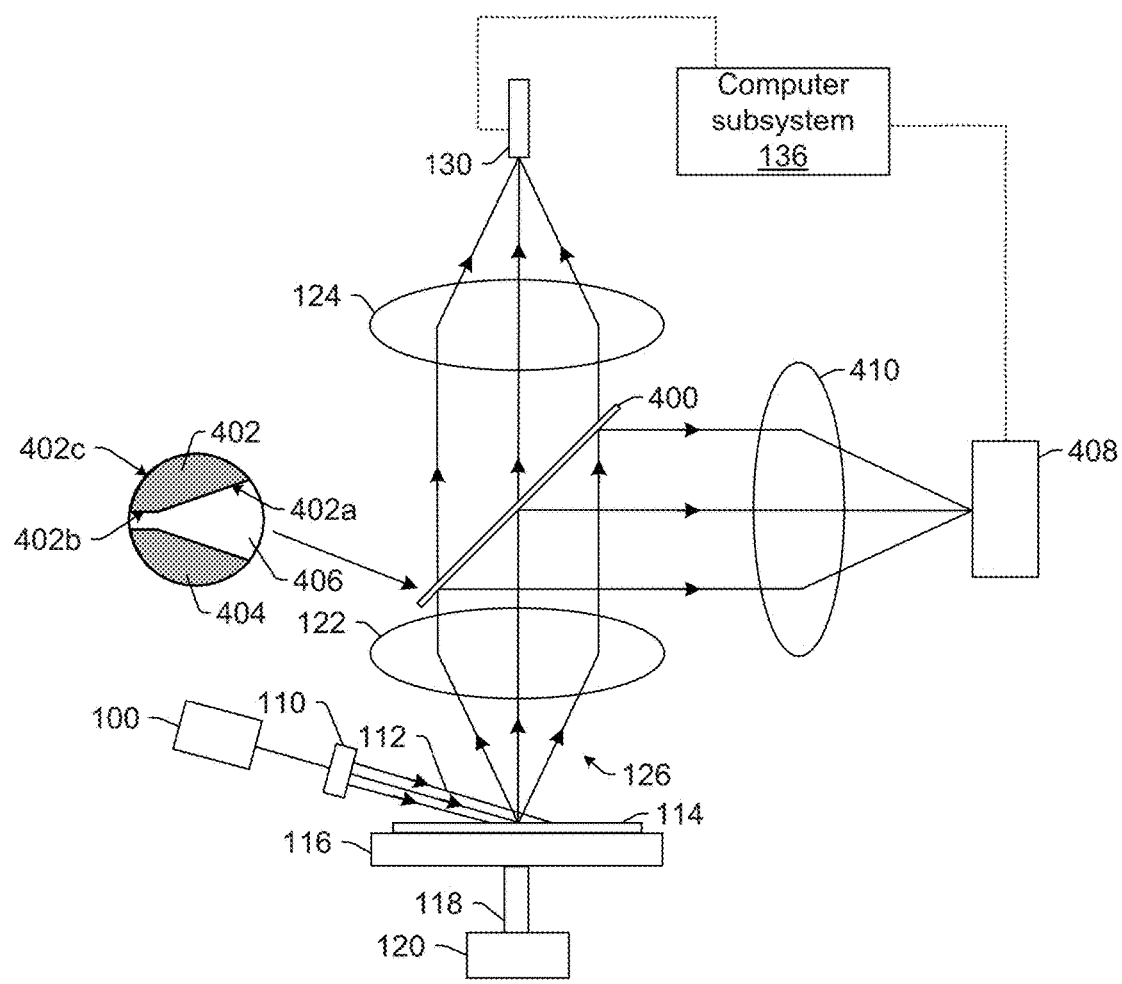

The system configurations described above may be implemented in a number of different embodiments that will be described here. For example, in one embodiment, the system includes an optical element configured to simultaneously and separately divide the light scattered from each of the areas collected in different segments of a collection NA of the collections subsystem, the two or more sensors are configured to detect one of the different segments, and the system includes another two or more sensors configured to detect another of the different segments. One such embodiment is shown in FIG. 4 in which optical element 400 is positioned in the path of the light collected by scattered light collector 122. Only scattered light 126 from only one of the multiple illuminated areas on the wafer is shown in FIG. 4 for clarity. The optical element may be preferably positioned at a Fourier plane or a conjugate of the Fourier plane of the collection subsystem. "At a Fourier plane" or "at a conjugate of the Fourier plane" is defined herein to mean not only just at exactly the Fourier plane or at exactly the conjugate of the Fourier plane. Instead, those terms are intended to mean "at or near a Fourier plane" and "at or near a conjugate of the Fourier plane," respectively. An optical element as described herein can be considered to be "at or near a Fourier plane" if it is positioned at the exact location of the Fourier plane or at a position that is within about 5% error of the exact location of the Fourier plane (due to whatever error sources are in the system and/or physical constraints in the system). "At or near a conjugate of the Fourier plane" can be described in a similar manner.

The optical element may include various optical elements such as an aperture, a mask, an apertured mirror, a liquid crystal display (LCD) element, or a micro-mirror array. In one such example, a suitable aperture may be formed by cutting out a portion of a folding mirror such that one portion of the mirror transmits light while another portion of the folding mirror reflects light. In another such example, an apertured mirror can be manufactured by forming a masking coating of metal film(s) and/or dielectric film(s) on a transparent substrate. The segmentation of the collection NA can also be realized by using other beam splitting optical elements such as prisms with various facet orientations to refract the light in different directions. Other means of segmenting the collection NA are also possible, including digital micromirror devices such as those commonly used in digital light projectors.

The optical element (and other optical elements described herein) is used to separate the collection NA into different segments such that the scattered light in the different segments can be directed to different sensors or channels of the system. For example, as described above, the optical element may have one portion that reflects light and another portion that transmits light. Therefore, the optical element may separate the collection NA into two segments, one segment of which is directed into one channel by reflection and another segment of which is directed into another channel by transmission.

In one embodiment, as shown in cross-section in FIG. 4, the optical element may include transmissive portions 402 and 404 that correspond to one segment of the collection NA and reflective portion 406 that corresponds to another different and mutually exclusive segment of the collection NA. Reflective portion 406 may reflect substantially all of the light in the segment of the collection NA corresponding to portion 406 (i.e., portion 406 may have roughly 0% transmission of the scattered light), while portions 402 and 404 may transmit substantially all of the light in the segment of the collection NA corresponding to portions 402 and 404 (i.e., portions 402 and 404 may having roughly 100% transmission of the scattered light). In this manner, the entire collection NA can be separated into two mutually exclusive portions.

As described above, the different portions of the optical element correspond to the different segments of the collection NA into which the scattered light is separated by the optical element. In addition, as shown in FIG. 4, portions 402 and 404 are mirror symmetrical to each other about an incident plane of the illumination subsystem. Furthermore, portions 402 and 404 may correspond to one of the different segments of the collection NA. In this manner, one of the different segments may include two individual segments (corresponding to portions 402 and 404) that are mirror symmetrical to each other about an incident plane of the illumination subsystem. In addition, as shown in FIG. 4, each of portions 402 and 404 is spaced from the incident plane. Furthermore, each of the portions can be defined by first, second, and third sides, which will be described with respect to portion 402. In particular, portion 402 includes first side 402a, second side 402b, and third side 402c. First side 402a is linear and arranged at an angle with respect to the incident plane. Second side 402b is linear, is substantially parallel to the incident plane, and is substantially shorter than the first side. In addition, third side 402c is curved. As shown in FIG. 4, portion 404 is also defined by these three sides.

As further shown in FIG. 4, the two or more sensors (represented by sensor 130) are configured to detect one of the different segments, and the system includes another two or more sensors (represented by sensor 408) configured to detect another of the different segments. Sensor 408 and the other two or more sensors may be further configured as described herein. In addition, the two or more sensors and the other two or more sensors may be the same type of sensors or different types of sensors. For example, the two or more sensors and the other two or more sensors may be selected depending on the amount of light expected to be directed to each of the sensors. In addition, optical elements such as those described further herein may be coupled to the other two or more sensors. For example, as shown in FIG. 4, refractive optical element 410 may be configured to image light reflected by optical element 400 onto sensor 408 and any of the other two or more sensors included in the system. The system shown in FIG. 4 may be further configured as described herein.

In these and any other embodiments described herein, each channel may end up with a different shape and extent, in pixels, of the point spread function on the corresponding sensors. Therefore, in order to maximize the sensitivity to anomalies, different analog and/or filtering techniques may be applied to each individual sensor output. In particular, the expected shape of the point spread function, based on the Fourier plane apertures, can be calculated in advance of an inspection, and the appropriate filter coefficients can then be applied during the inspection.

In one such embodiment, the system is configured to alter or replace the optical element depending on the one of the different segments that is to be detected by the two or more sensors and the other of the different segments that is to be detected by the other two or more sensors. For example, the system may include a flexible aperture collection space in an area mode inspection system with multiple configurable channels. One improvement of this area inspection system over other inspection systems is the selective, and configurable, collection of surface scatter to enhance the detection of particles and defects. The system may be configured to alter or replace the optical element in any suitable manner.

In another embodiment, the system includes an optical element configured to simultaneously and separately divide the light scattered from each of the areas collected in different segments of a collection NA of the collection subsystem, the two or more sensors are configured to detect one of the different segments using one portion of the two or more sensors and to detect another of the different segments using a different portion of the two or more sensors, and the one portion and the other portion of the two or more sensors do not overlap with each other and are not contiguous on the two or more sensors. For example, the system may be configured for separating scattered light by angle in the collection space and reimaging the light into two separate patches on a single sensor. In particular, the number of active pixels on the sensor may be controlled during or before the scan either in conjunction with or independent of the illumination shape and extent. All or some of the elements on a particular sensor may be utilized. One part of one sensor, including a number of elements, may receive scattered light from one range of solid angles, and another part of that sensor may receive scattered light from another range of solid angles. For example, if a sensor includes 1000×1000 individual elements, 1000×500 of the elements may receive an image of the scattered light generated between 40 and 60 degrees forward azimuth. The second half (1000×500) of the sensor may receive an image of the scattered light from the surface generated between 120 and 160 azimuth. In some cases, portions of the scattered light imaged onto the sensor surface may be inverted, and other portions may remain uninverted. One additional configuration is to read the sensor data from both ends of each column (e.g., row 1 and row N) simultaneously, which in some sensors can effectively double the sensor data rate.

Each of the system embodiments described herein may be further configured as described in International Application Publication No. 2012/082501 by Zhao et al. filed Dec. 7, 2011, which is incorporated by reference as if fully set forth herein.

Figure 5:
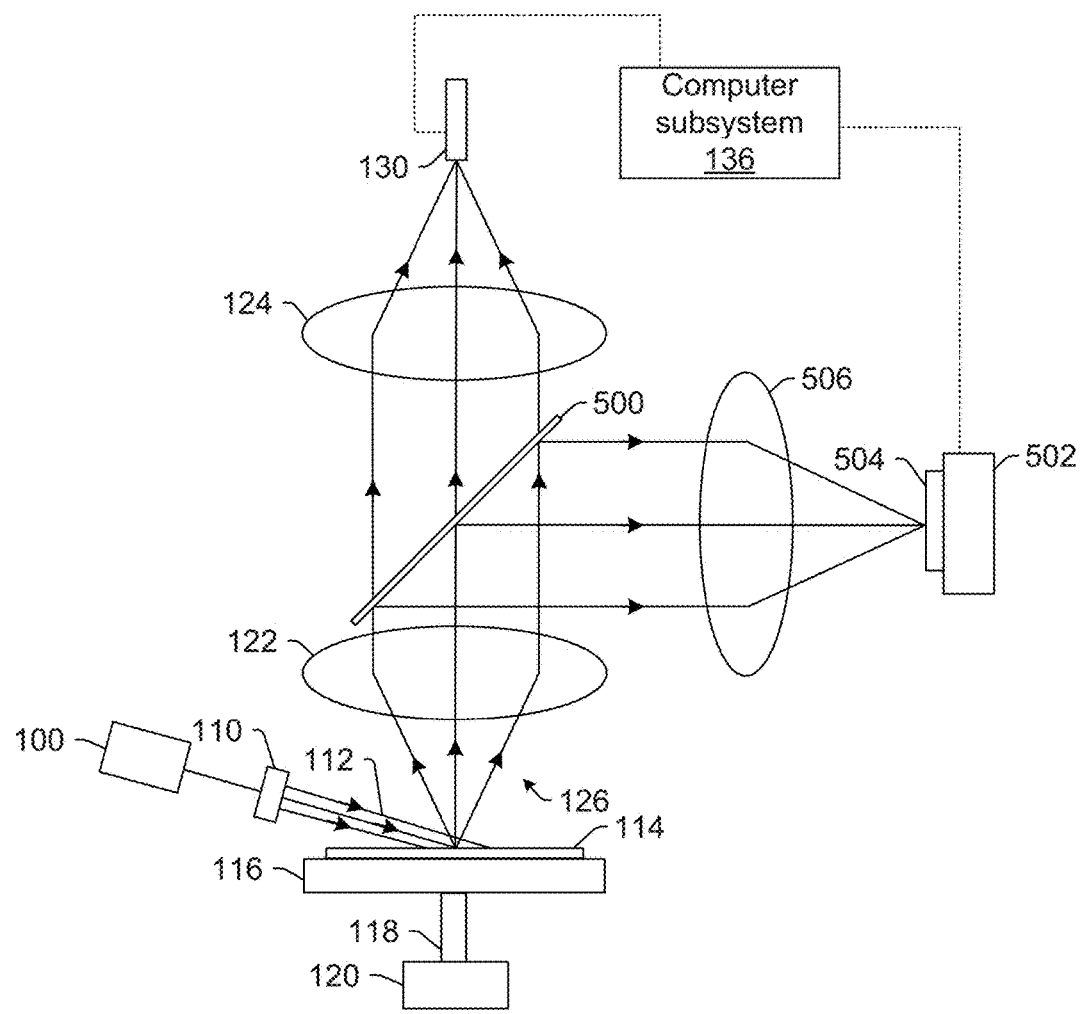

In a further embodiment, the system includes an additional two or more sensors that include image intensifiers, the collection subsystem is configured to simultaneously and separately image the light scattered from each of the areas to the additional two or more sensors, the additional two or more sensors generate additional output responsive to the scattered light, and the computer subsystem is configured to detect the defects on the wafer using the additional output instead of the output when sensor electronic noise dominates total channel noise in the two or more sensors. For example, such an embodiment may include one or more flexible apertures as described above to optimize performance, cost, and reliability of the sensors. In one such embodiment, the system shown in FIG. 5 includes optical element 500 configured to simultaneously and separately image the light scattered from each of the areas to an additional two or more sensors (represented in FIG. 5 by sensor 502). Optical element 500 may be further configured as described herein. However, optical element 500 may also include a beam splitter that is configured to transmit a portion of the scattered light across the entire collection NA of the collection subsystem and to reflect a portion of the scattered light across the entire collection NA of the collection subsystem. For example, optical element 500 may be a simple 70/30 beam splitter. In addition, as described above, the sensor type and size for each channel may be selected based on the scattered background characteristics expected in that channel as well as the defects of interest sensitivity requirements in that channel. In some such cases, when sensor electronic noise dominates the total channel noise, an intensified sensor may be desirable. However, when another noise source besides sensor read-out noise dominates, a non-intensified sensor may be preferred. For example, the additional two or more sensors (represented by sensor 502 in FIG. 5) each include an image intensifier (represented by image intensifier 504 in FIG. 5), and the two or more sensors (represented by sensor 130 in FIG. 5) may not include any image intensifiers. Such a configuration may also be reversed such that the two or more sensors (represented by sensor 130 in FIG. 5) each includes an image intensifier (not shown in FIG. 5) and such that the additional two or more sensors (represented by sensor 502 in FIG. 5) do not include arty image intensifiers. In this manner, various optical elements described herein (e.g., a flexible aperture and mirror arrangement) may be used to direct light to intensified sensor(s) When the light is low and other non-intensified sensor(s) when the light is high. When the point spread function projected onto a particular sensor is expected to be large due to the spatial filtering, a lower overall sensor resolution could be permitted, in accordance with sampling theory. For example, in some channels, the illuminating patch on the wafer, when imaged through the collection optics and spatial filter, may be approximately 2000 point spread functions in extent. In other channels, with different spatial filters restricting the collection NA, the image of the illuminating patch on the wafer may be 1000 point spread functions in extent. In this way, the system may be optimized with lower cost sensors in channels where other noise sources dominate in order to reduce operating costs. Furthermore, intensified sensors generally have shorter lifetimes than non-intensified sensors so this particular configuration allows improved system reliability as well. The system shown in FIG. 5 may be further configured as described herein. For example, as shown in FIG. 5, the collection subsystem may include refractive optical element 506 that is configured to image the scattered light from optical element 500 to the additional two or more sensors. Refractive optical element 506 may be further configured as described herein. The system shown in FIG. 5 may be further configured as described herein.

Such an embodiment may also or alternatively include one or more flexible apertures as described above to direct the scattered light to the most appropriate sensor. For example, one sensor may be optimized for substantial light scattering while another sensor may be optimized for substantially low light scattering. In such a configuration, a sensor optimized for relatively low light scatter, e.g., an image intensified sensor, can be damaged by substantial scatter and is not even necessary to achieve optimal sensitivity with relatively large background. As such, during sonic portions of a scan, the optical element may be configured to direct one portion of the scattered light to a sensor optimized for substantial light scattering and to direct another, different portion of the scattered light to a different sensor that is optimized for low-light scattering. In a different example, the optical element may be configured to direct all of the scattered light to only one of multiple sensors included in the system, and the sensor to which the scattered light is directed may change during the scan.

In another embodiment, the system includes an additional two or more sensors that are configured for photon counting, the collection subsystem is configured to simultaneously and separately image the light scattered from each of the areas to the additional two or more sensors, the additional two or more sensors generate additional output responsive to the scattered light, and the computer subsystem is configured to detect the defects on the wafer using the additional output. For example, such an embodiment may include multiple flexible apertures as described above to optimize performance, cost, and reliability of the sensors. In some such cases, so-called photon counting techniques may be employed for one or more of the sensors included in the system. Such an embodiment may be configured as shown in FIG. 4 or 5 with the additional two or more sensors (represented by sensor 408 or the combination of sensor 502 and image intensifier 504, respectively) replaced with sensors that are configured for photon counting. The sensors that are configured for photon counting may be any suitable such sensors known in the art, such as avalanche photo diodes.

In one embodiment, the system includes a MEMS-based optical switching device positioned between the collection subsystem and the two or more sensors. For example, there exist relatively fast MEMS-based optical switching devices that can be reconfigured between every laser pulse. One or more of these may be disposed at a suitable location in the collection optics. For example, optical elements 400 and 500 shown in FIGS. 4 and 5, respectively, may be replaced by a MEMS-based optical switching device. The MEMS-based optical switching device may include any suitable such element known in the art.

In one such embodiment, the system includes an additional two or more sensors, the illumination subsystem is configured to simultaneously form the multiple illumination areas using pulses of light, the light scattered from each of the areas includes pulses of scattered light, and the optical switching device is configured to direct a first set of the pulses of scattered light generated by a first set of the pulses of light to the two or more sensors and a second set of the pulses of scattered light generated by a second set of the pulses of light, subsequent to the first set of the pulses of light, to the additional two or more sensors. For example, if optical elements 400 and 500 shown in FIGS. 4 and 5, respectively, are replaced by an optical switching device as described above, then the additional two or more sensors represented by detector 408 in FIG. 4 and detector 502 in FIG. 5 may be used for the additional two or more sensors in this embodiment. In this manner, the optical switching device in the collection optics may direct alternate frames onto alternate sensors to save cost. In this way, if a relatively high repetition rate laser is available, but the data rate and/or frame rate of a particular sensor type is limited, the scattered light generated by subsequent laser pulses can be directed to alternate sensors by reconfiguring the MEMS device in between laser pulses. For example, scattered light generated by a pulsed laser at frequency f may be directed to an electro-optic beam splitter operating at frequency f. The electro-optic beam splitter may be used for relatively fast switching of scattered light alternatively between two sensors, each sensor with an effective frame rate of f/2. Therefore, if a sensor has a limited readout rate, and the system does not allow two or more sensors to be placed side-by-side for cost, packaging, or other reasons, then an optical switching element of some type can allow the data rate to be multiplied (e.g., doubled, tripled, etc.) by directing the light onto different sensors as a function of time. Limitations of individual sensor components can be overcome. Such embodiments work particularly well with a Q-switched laser that has a repetition rate of about 2 kHz to about 40 kHz (e.g., low enough to admit the use of optical switches).

In another such embodiment, the illumination subsystem is configured to simultaneously form the multiple illumination areas using pulses of light, the light scattered from each of the areas includes pulses of scattered light, the optical switching device is configured to simultaneously and separately divide the pulses of scattered light from each of the areas collected in different segments of a collection NA of the collection subsystem, and the optical switching device is configured to direct only one of the different segments of a first set of the pulses of scattered light generated by a first set of the pulses of light to the two or more sensors and then to direct only another one of the different segments of a second set of the pulses of the scattered light generated by a second set of the pulses of light, subsequent to the first set of pulses of light, to the two or more sensors. For example, one sensor could receive and process different sections of the scattering light hemisphere on subsequent laser shots. The MEMS device will be configured to spatially select and direct particular bundles of scattered light to the sensor. In particular, the MEMS device may be configured to function like optical element 400 described above. The field size of the imaging objective can be reduced by at least a factor of two with this configuration, which provides a substantial cost savings, even after accounting for the extra expense of the switching device.

In some embodiments, the illumination subsystem is configured to simultaneously form the multiple illumination areas using pulses of light, the light scattered from each of the areas includes pulses of scattered light, and the two or more sensors are synchronized in time relative to the pulses of light to detect only the pulses of scattered light with predetermined arrival times. In one such embodiment, the pulses of scattered light with the predetermined arrival times include fluorescence or photoluminescence. For example, the embodiments described herein may utilize camera shutter synchronization to look for fluorescence, etc. In particular, each channel and/or sensor may be synchronized in time relative to the laser pulse to capture only photons with specific arrival times. In this way, time-dependent effects such as fluorescence or photoluminescence may be observed independently of the scattered light generated by classical means thereby providing additional information regarding the surface and/or defects of interest.

In another embodiment in which the multiple illumination areas are formed using pulses of light, the sensor acquisition and scanning subsystem rotation and/or translation rates may be synchronized to this pulse frequency (or vice versa) according to "flash on the fly" techniques. Some spatial overlap between subsequent laser pulses can be desirable as previously described.

In any of the embodiments in which the scattered light is split between two or more channels of the inspection system, each channel may include separate anamorphic optical element(s) positioned between the Fourier plane and the sensor(s) of the channels. The separate anamorphic optical element(s) in each of the channels may be different and may depend on the characteristics of the scattered light (e.g., the segment of the scattered light) that the channels are being used to detect.

Each of the embodiments described above may be further configured as described herein.

Figure 9:
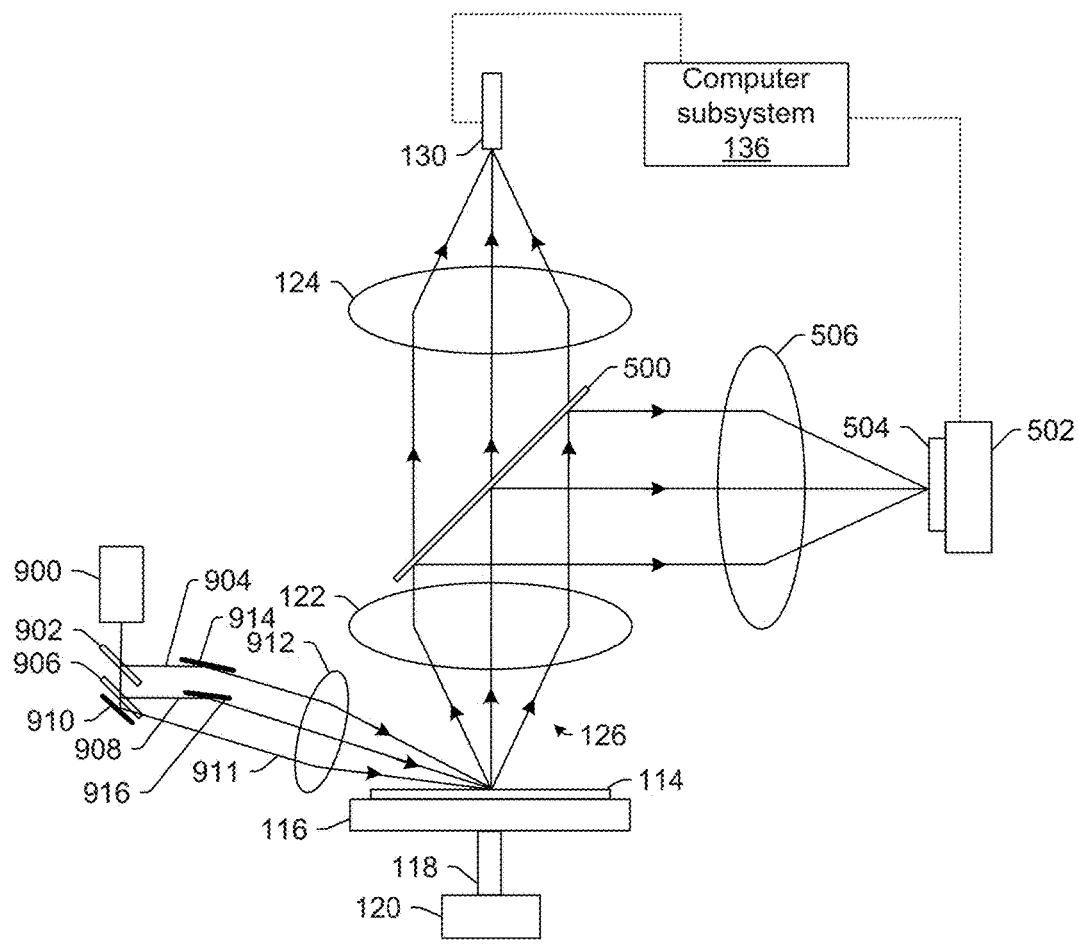
FIG. 9 is a schematic diagram illustrating a side view of one embodiment of a system configured to inspect a wafer.

Another embodiment relates to another system configured to inspect a wafer. This system includes an illumination subsystem configured to direct multiple light beams to substantially the same area on a wafer. The multiple light beams have substantially the same wavelength and polarization characteristics. For example, two or more light beams of the same wavelength and polarization cannot be combined losslessly, but the two or more light beams can be made parallel to each other (e.g., using the folding mirrors shown in FIG. 9). In some embodiments, the multiple light beams are laser beams. In this manner, the illumination subsystem may have a multiple laser beam configuration. In another embodiment, the multiple light beams are generated by only one single laser of the illumination subsystem. For example, the multiple illumination beams used for area mode may be generated within a single laser. Some lasers have frequency conversion crystals whose lifetime can be limited by the intensity of the spot incident on the crystal. With multiple simultaneous incident spots the lifetime of the crystal may be extended. In one such embodiment shown in FIG. 9, the illumination subsystem may include only one single light source 900 that may be a laser. The laser may include any of the lasers described herein or any other suitable laser known in the art.

Light from the light source may be directed to beam splitter 902 of the illumination subsystem, which is configured to split the light beam from the light source into first light beam 904 and another light beam. The illumination subsystem may also include beam splitter 906, which is configured to split the light beam from beam splitter 902 into second light beam 908 and another light beam. Beam splitters 902 and 906 may include any suitable beam splitters known in the art. The illumination subsystem may also include reflective optical element 910, which is configured to reflect the light beam from beam splitter 906 as third light beam 911 to refractive optical element 912 of the illumination subsystem. The illumination subsystem may also include reflective optical element 914 positioned in the path of the first light beam and reflective optical element 916 positioned in the path of the second light beam. Reflective optical elements 914 and 916 are configured to direct the first and second light beams, respectively, to refractive optical element 912 such that the first, second, and third light beams are substantially parallel to each other when they are incident on refractive optical element 912. In this way, reflective optical elements positioned in the path of each of the light beams may control the angle at which each of the light beams is directed to the refractive optical element and the refractive optical element controls the angle at which each of the light beams is directed to the wafer. Reflective optical elements 910, 914, and 916 may include any suitable reflective optical elements known in the art, and refractive optical element 912 may include any suitable refractive optical element known in the art. The system shown in FIG. 9 may be further configured as described herein.

In another embodiment, light source 900, beam splitters 902 and 906 and reflective optical elements 910, 914, and 916 may be replaced with a single light source such as a laser from which multiple beams (e.g., three) emanate. The multiple beams emanating from the light source may be directed to refractive optical element 912 at substantially the same angle and then may be directed to wafer by the refractive optical element. Such an embodiment may be further configured as described herein.

If two or more (e.g., three) light beams are arranged to be parallel to each other, they can be focused by a lens (e.g., refractive optical element 912) to the same location on the wafer. Such a configuration is allowed for spot sizes on the wafer of 100 um or more. For example, in some such embodiments, the illumination subsystem may include a lens (e.g., refractive optical element 912) configured to direct the multiple beams onto the wafer, and the lens can have an NA of about 0.1 or higher so that it can focus a number of relatively low NA input beams simultaneously. In one such example, for an illumination subsystem that includes a 266 nm laser, a spot size of about 100 um to about 1 mm on the wafer requires only an NA of less than 0.01 to form the spot. Due to the relatively low NA of the lens, all beams can illuminate the same patch on the wafer with approximately the same size. In contrast, for the case of an approximately 1 um spot, the tens NA would need to be 0.5 or greater, so a single lens could not inject multiple beams of the same wavelength. In general, any number of beams or light sources may be used by the illumination subsystems described herein.

In one embodiment, the multiple light beams are directed to the substantially the same area on the wafer at substantially the same polar angles and different azimuth angles. In this manner, the multiple tight beams (e.g., laser beams) may illuminate the wafer at nearly the same angle of incidence. For example, one laser beam may be incident at 55 degrees polar angle and 0 degrees azimuth angle, and a second laser beam may be incident at 55 degrees polar angle and 2 degrees azimuth angle. Nearly the same angle of incidence and polarization vector may be used such that the scattered light generated by each light beam has the same characteristic and polarization state to thereby be effectively filtered in the collection subsystem. Light beams of identical wavelengths cannot be combined and injected at the exact same angle, but injection within 5 degrees of each other is possible and will result in nearly the same surface scatter characteristics so that sensitivity will not be compromised. In another example, if the center beam is incident on the wafer at about X degrees polar angle, the two other beams can be incident on the wafer at about X−2 degrees polar angle and about X+2 degrees polar angle, for example, and there will be substantially little difference in the resulting surface scatter from each of the beams.

In another embodiment, the multiple light beams are directed to the substantially the same area on the wafer simultaneously. For example, although the multiple light beams have substantially the same wavelength and polarization characteristics, as described above the multiple light beams can be simultaneously directed to substantially the same area on the wafer simultaneously by splitting light from a single light source into multiple light beams that are directed to the wafer at slightly different azimuth and/or polar angles or by using multiple light sources that produce multiple light beams that are directed to the wafer at slightly different azimuth and/or polar angles. Directing multiple light beams having the same wavelength and polarization characteristics to the wafer simultaneously has a number of advantages described further herein.

Figure 10:
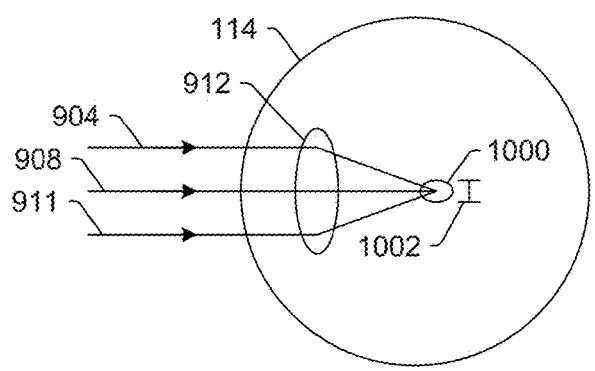
FIG. 10 is a schematic diagram illustrating a plan view of one embodiment of multiple light beams being directed to substantially the same area on a wafer at substantially the same polar angles and different azimuth angles.

In another embodiment, the multiple light beams illuminate the substantially the same area on the wafer in area illumination mode. For example, the illumination subsystem may have a multiple illumination beam configuration for area mode. In some embodiments, the substantially the same area on the wafer has a lateral dimension of greater than 50 microns. For example, as shown in FIG. 10, multiple light beams 904, 908, and 911 may be directed to substantially the same area 1000 on wafer 114 by refractive optical element 912. Lateral dimension 1002, which is the shortest dimension of substantially the same area 1000, may be greater than 50 microns. In addition, although substantially the same area 1000 may have an elliptical shape on the wafer as shown in FIG. 10, substantially the same area may have any other shape (e.g., rectangular) on the wafer described further herein.

In another embodiment, the multiple light beams are pulsed light beams, and the illumination subsystem is configured to direct one of the multiple light beams to the substantially the same area on the wafer later than another of the multiple light beams is directed to the substantially the same area by the illumination subsystem such that the pulsed light beams illuminate the substantially the same area as one continuous pulse of light having a duration longer than each of the pulsed light beams. In an additional embodiment, the multiple light beams are pulsed light beams, and the illumination subsystem is configured to direct one of the multiple light beams to the substantially the same area on the wafer later than another of the multiple light beams is directed to the substantially the same area by the illumination subsystem such that a peak pulse power incident on the wafer due to the multiple light beams is less than if the multiple light beams were directed to the substantially the same area on the wafer at the same time. In this manner, these embodiments have the advantage of effectively being able to stretch out pulse duration, compared to a single light beam. In the multiple illumination beam configurations for area mode, the pulse duration may be stretched out to reduce the peak pulse power incident on the wafer thereby reducing the probability of damaging the wafer. In one particular example, assuming each of the lasers or light sources is a pulsed tight source with a repetition rate between about 2 kHz and 50 kHz and a pulse duration between about 10 ns and 200 ns, if all of the pulses are incident on the wafer at the same time, then the energy density will be substantially high. But since the wafer is moving substantially slowly compared to the pulse duration, the pulses can be spread out in time and still basically expose the same area. For example, a first pulse may be incident on the wafer at time to, a second pulse may be incident on the wafer at time t0+t1, and a third pulse may be incident on the wafer at time t0+2*t1. Therefore, as long as in the time interval between the first and the last pulse (e.g., 2*t1 in the above example) the wafer, as referenced to the sensor(s), has not moved by more than one sensor pixel, the overall signal-to-noise will be approximately the same as if all of the pulses were incident on the wafer at the same time, but the peak power density incident on the wafer will he reduced so as to not damage the wafer.

Figure 12:
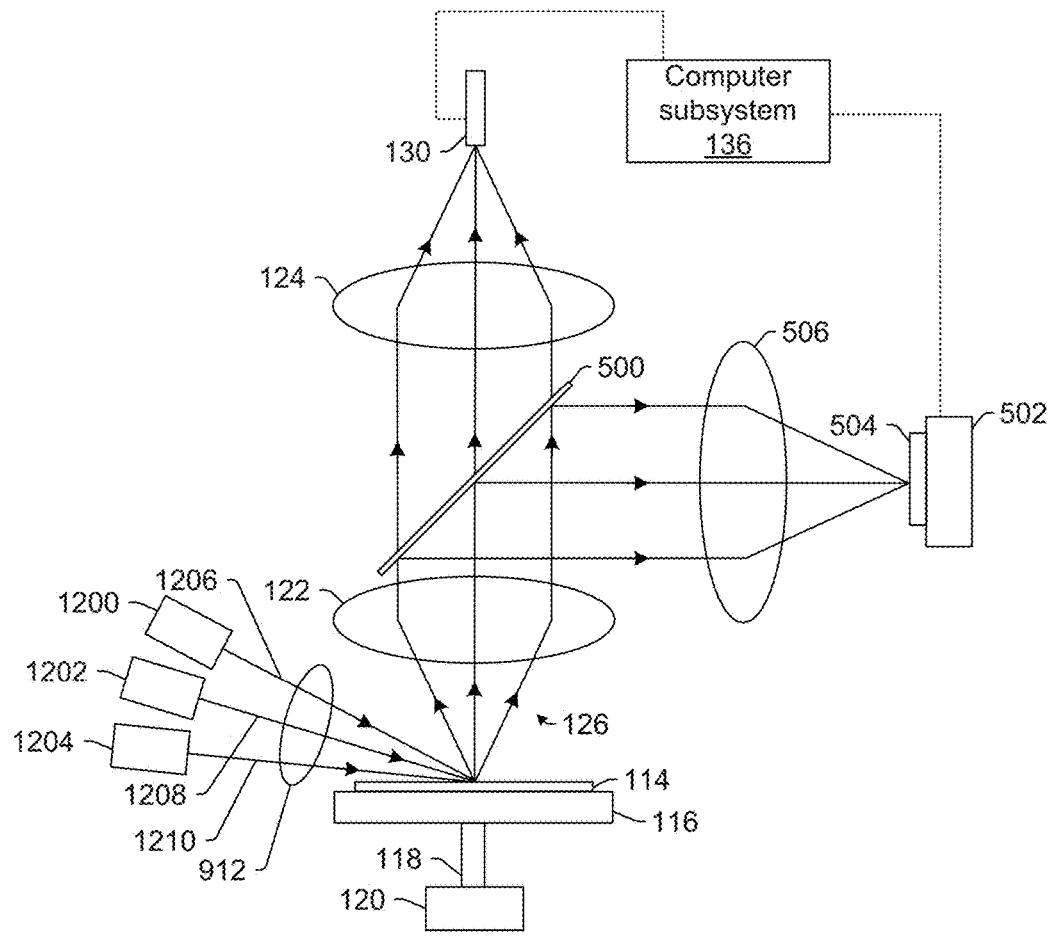
FIG. 12 is a schematic diagram illustrating a side view of one embodiment of a system configured to inspect a wafer.

In another embodiment, the multiple light beams are generated by multiple lasers of the illumination subsystem. For example, the multiple illumination beams used for area mode may be generated from multiple lasers. In one such embodiment shown in FIG. 12, the illumination subsystem may include lasers 1200, 1202, and 1204, which are configured to generate light beams 1206, 1208, and 1210, respectively. Lasers 1200, 1202, and 1204 may be identical lasers (i.e., lasers having the same make and model). Alternatively, lasers 1200, 1202, and 1204 may be different lasers (i.e., lasers having different makes and/or models), which generate light beams having the same wavelength and polarizations characteristics as each of the other light beams. As shown in FIG. 12, each of the light beams may be directed to wafer 114 by a single refractive optical element (e.g., refractive optical element 912), which may be configured as described above. The light beams shown in FIG. 12 may be directed to the wafer as described further herein (e.g., simultaneously or sequentially). In addition, the system shown in FIG. 12 may be further configured as described herein.

In some embodiments, the multiple light beams include one light beam generated by a light source of the illumination subsystem and another light beam formed by collecting light reflected from the substantially the same area on the wafer and directing the collected reflected light back to the substantially the same area on the wafer. Such an embodiment may be similar in function to using multiple light sources to produce the multiple light beams. For example, the multiple illumination beams used for area mode may be generated by recirculating multiple passes of the same light beam (by collecting the reflected light beam from the wafer and redirecting the light beam hack onto the wafer). In this manner, reflected light from a first pass may be collected and reformed into a second beam incident on substantially the same location of the wafer. In the multiple pass light beam option, the power available for each subsequent illumination pass will be reduced by the surface reflectivity and recirculating optics efficiency (therefore, most likely two additional beams is realistic although more recycled beams are certainly possible), but the effective illumination power can be enhanced by a factor of 50% or more. Note, that in general, these multi-beam techniques are challenging to implement on line or spot inspection systems as opposed to the systems described herein. One alternate illumination option is to use multiple laser beams of different wavelengths, to enable the more efficient detection of defects.

Figure 13:
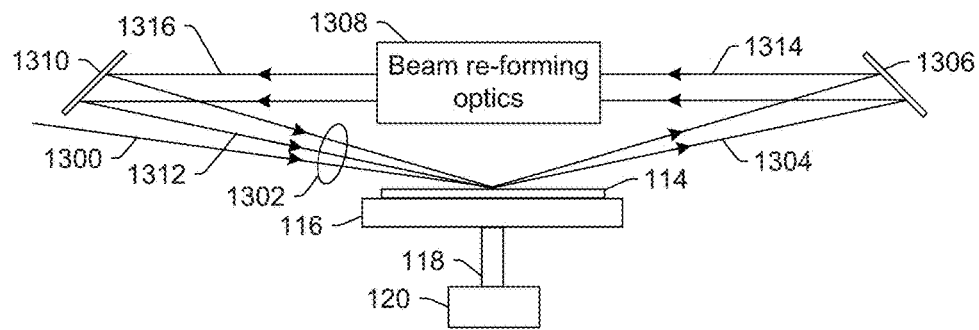
FIG. 13 is a schematic diagram illustrating a side view of one embodiment of multiple light beams that include one light beam generated by a light source of an illumination subsystem and additional light beams formed by collecting light reflected from substantially the same area on the wafer and directing the collected reflected light back to the substantially the same area on the wafer.

In one such embodiment, as shown in FIG. 13, the multiple light beams may include light beam 1300 generated by a light source (not shown in FIG. 13) of the illumination subsystem. Light beam 1300 may be generated by any of the light sources described herein. As shown in FIG. 13, light beam 1300 is directed to wafer 114 by refractive optical element 1302, which may be configured as described further herein (e.g., with respect to refractive optical element 912). Light 1304 specularly reflected from the substantially the same area on the wafer is collected by reflective optical element 1306 of the illumination subsystem, which directs the collected reflected light beam to beam re-forming optics 1308. Reflective optical element 1306 may include any suitable reflective optical element, and beam re-forming optics 1308 may include any suitable beam forming elements (e.g., anamorphic optical elements, field stops, spatial filters, polarization filters, and the like). Beam re-forming optics 1308 direct the collected reflected light beam to reflective optical element 1310, which directs the collected reflected light back to the substantially the same area on the wafer as light beam 1312. For instance, as shown in FIG. 13, light 1314 specularly reflected from wafer 114 may be collected by reflective optical element 1306, which directs the collected reflected light beam to beam re-forming optics 1308. Beam re-forming optics 1308 directs this collected reflected light back to the substantially the same area on the wafer as light beam 1316. The portion of the illumination subsystem shown in FIG. 13 may be included in any of the system embodiments described and shown herein.

In one embodiment, the illumination subsystem includes a frequency conversion laser, the multiple light beams include pulses of light, and the pulses of light directed to the substantially the same area on the wafer do not vary spatially over the duration of the pulses of light and have substantially constant intensity over the duration of the pulses of light. In one such embodiment, the illumination subsystem includes a beam shaping optical element coupled to the laser. In another embodiment, the illumination subsystem includes a frequency conversion laser, the multiple light beams include pulses of light, and the pulses of light directed to the substantially the same area on the wafer have substantially constant intensity over the duration of the pulses of light. Such embodiments may be further configured as described herein.

The system also includes a scanning subsystem configured to scan the multiple light beams across the wafer. The scanning subsystem may be further configured as described herein. In addition, the system includes a collection subsystem configured to image light scattered from the substantially the same area on the wafer to a sensor. The sensor generates output responsive to the scattered light. The collection subsystem and the sensor may be further configured as described herein.

A zoom lens group within the collection optics allows for different size areas on the wafer to be imaged onto the same sensor (or sensors) depending on the speed of inspection and/or the sensitivity of inspection required. When a relatively fast inspection (more wafers per hour) is desired, a larger area of the wafer (say 2 mm×2 mm) is imaged onto a sensor (or sensors) of fixed size. When a higher sensitivity (typically lower speed) inspection is desired, a smaller area is imaged onto the sensor(s) after a magnifying element is inserted into or moved in the collection optics path. This change in speed or sensitivity can in general be performed both during an inspection and before an inspection. The area of the illumination spot is simultaneously increased to expose the appropriate region. The intensity of the illumination spot preferably stays the same when the illumination spot area changes although it may be increased to improve inspection sensitivity to the extent that laser-induced damage can be avoided (the multiple-beam techniques described previously can reduce the probability of laser induced damage) Alternatively, a smaller zoom factor in the collection optics may be employed in conjunction with a larger illuminated area, and additional sensors may be used to image this larger portion of the wafer thereby improving inspection speed while maintaining inspection sensitivity.

In one embodiment, the collection subsystem includes a scattered light collector having a resolution that is not fully diffraction-limited. Such an embodiment may be further configured as described herein.

In some embodiments, the illumination subsystem is configured to vary the multiple light beams directed to the substantially the same area on the wafer as a function of time, the collection subsystem is configured to image the light scattered from multiple areas on the wafer to the sensor, and the sensor and a light source of the illumination subsystem are gated in sync with one another. In this manner, the system may be configured for time-domain multi-spot inspection in area mode. For example, the illumination profile may not only be varied as a function of position as described above, but also as a function of time. Scattered light from different portions of the wafer may be received by the same sensor, and it may be advantageous to gate the illumination and the sensor together (which we will refer to as time-domain multi-spot) in order to improve throughput, defect capture, or lessen the probability of surface damage. The different illumination profiles in time can be generated by lasers or laser beams incident on the wafer from different azimuth and/or polar angles. One substantial advantage of time-domain multi-spot inspection, relative to inspecting the same wafer twice with two different optical configurations, is the fixed time overhead associated with inspecting each wafer, for example, loading, unloading, registering, acceleration, and deceleration is only applied once, thereby increasing overall throughput.

In one such embodiment, the multiple light beams are directed to the substantially the same area on the wafer at different azimuth angles, different polar angles, or different azimuth and polar angles. For example, although as described above, the multiple light beams may be simultaneously directed to the substantially the same area on the wafer at different azimuth angles and the same polar angles, both the azimuth and polar angles at which the multiple light beams are directed to the wafer can be varied (e.g., by altering a position of the reflective optical elements shown in FIG. 9 or the multiple light sources shown in FIG. 12) over time.

In another such embodiment, the illumination subsystem is configured to alter the wavelength and polarization characteristics of the multiple light beams, and the multiple light beams directed to the substantially the same area on the wafer as the function of time have different wavelength characteristics from each other, different polarization characteristics from each other, or different wavelength and polarization characteristics from each other. For example, although as described above, the multiple light beams may have the same wavelength and polarization characteristics, both the wavelength and polarization characteristics of the multiple light beams can be varied over time (e.g., using one or more polarizers having time-dependent polarization characteristics (e.g., due to rotation of the polarizer(s)) and/or using one or more wavelength filters having time-dependent wavelength characteristics)

In one embodiment, the multiple light beams include pulses of light, the scattered light includes pulses of scattered light, and the sensor is synchronized in time relative to the pulses of the light to detect only the pulses of scattered light with predetermined arrival times. In one such embodiment, the pulses of scattered light with the predetermined arrival times include fluorescence or photoluminescence. Such embodiments may be further configured as described herein.

The system further includes a computer subsystem configured to detect defects on the wafer using the output of the sensor. The computer subsystem may be configured as described further herein.

For substrates where the scattering intensity of the entire surface exceeds a predetermined value in one or more of the collected light scattering channels, optical attenuation or the optical or electronic gain of the particular sensors associated with those channels may be adjusted prior to inspection to maximize inspection sensitivity or dynamic range.

Figure 11:
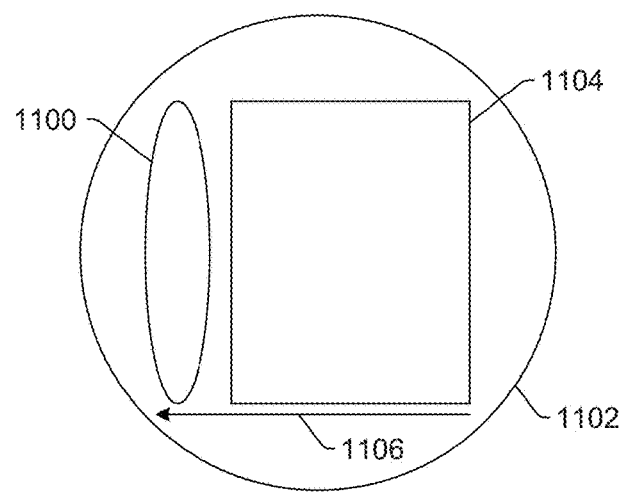
FIG. 11 is a schematic diagram illustrating a plan view of one embodiment of multiple light beams having different shapes and sizes on the wafer from each other.

In one embodiment, the multiple light beams are pulsed light beams, the illumination subsystem is configured to direct a first of the multiple light beams to the substantially the same area on the wafer earlier in time than a second of the multiple light beams is directed to the substantially the same area by the illumination subsystem, the first and second of the multiple light beams have different shapes and sizes on the wafer from each other, and the computer subsystem is configured to use the output responsive to the scattered light from the substantially the same area due to illumination by the first of the multiple light beams to determine if the second of the multiple light beams should be directed to the substantially the same area. Such an embodiment may be advantageous because the leading beam (e.g., the first multiple light beam) may be used to sense relatively large particles on the wafer thereby preventing damage to the wafer that can be caused by illuminating the relatively large particles with the main inspection beam (e.g., the second multiple light beam). In addition, the leading beam may be used to detect if the haze on the wafer is getting too high thereby preventing damage to the sensor that can be caused by light scattering due to the haze that could exceed the damage threshold of the sensor or the usable dynamic range of the sensor. FIG. 11 shows one example of a secondary beam illuminating spot 1100 on wafer 1102 ahead of spot 1104 illuminated by the main inspection beam. The relatively thin spot of the secondary beam has the advantage of not increasing the optics field of view very much. As shown in FIG. 11, the two beams may have markedly different profiles, in time and in space, on the wafer. The direction of travel of the spots on the wafer is indicted by arrow 1106. As described further herein, the light scattered from the illumination area of the inspection beam may be imaged onto multiple sensors, and the illumination used for the inspection beam may be pulsed illumination. Depending on the scattered light from the secondary beam, the computer subsystem may produce a trigger that is a signal to the light source to not issue a pulse that would be used for the inspection beam.

The scattered light from the substantially the same area due to illumination by the first and second of the multiple light beams may be detected by the same sensor. However, the scattered light from the substantially the same area due to illumination by the first and second of the multiple light beams may be detected using different sensors. In this case, the sensor described above would be used to detect the scattered light from the substantially the same area due to illumination by the second of the multiple light beams, and another sensor would be used to detect the scattered light from the substantially the same area due to illumination by the first of the multiple light beams. The other sensor may be further configured as described herein.

In this manner, elements of the system used for inspection (or an additional optical subsystem included in the system) may be configured to detect relatively large defects or other light scattering events, prior to scattered light from these events being incident on the area inspection sensor(s). For example, substantial amounts of scattered light may saturate or damage an image sensor or exceed the capability of the sensor to quantitatively measure the scatter. It is preferable to reduce the incident intensity prior to the inspection of a scattering area. The system (or the additional optical subsystem) scans the wafer in advance of the main inspection spot and corresponding sensor area, and if substantial scattered light is detected, a control signal reduces (e.g., eliminates)) the power incident on that area of the surface. Alternatively, attenuation of the scattered light may be added in the collection subsystem, or the optical or electronic gain of the sensors or intensified elements may be adjusted temporarily (e.g., using electro-optic shutter(s)).

In one such embodiment, the illumination subsystem includes a Q-switched laser, and if the computer subsystem determines that the second of the multiple light beams should not be directed to the substantially the same area, then the computer subsystem prevents the second of the multiple light beams from illuminating the substantially the same area. For example, as described above, depending on the scattered light from the secondary beam, the computer subsystem may produce a trigger that is a signal to the Q-switched laser to not issue a pulse that would be used for the inspection beam. However, the computer subsystem may prevent the second of the multiple light beams from illuminating the substantially the same area without controlling the Q-switched laser. For example, the computer subsystem may control an optical element such as a relatively fast electro optic shutter coupled to the Q-switched laser such that the optical element prevents a pulse generated by the Q-switched laser from illuminating the substantially the same area. In addition, the embodiments described above may be implemented with other pulsed light sources such as a CW laser or a mode locked laser.

In another embodiment, the multiple light beams are pulsed light beams, the illumination subsystem is configured to direct a first of the multiple light beams to the substantially the same area on the wafer earlier in time than a second of the multiple light beams is directed to the substantially the same area by the illumination subsystem, the first and second of the multiple light beams have different shapes and sizes on the wafer from each other, and the computer subsystem is configured to use the output responsive to the scattered light from the substantially the same area due to illumination by the first of the multiple light beams to determine a power of the second of the multiple light beams that should be directed to the substantially the same area. The power of the second of the multiple light beams determined by the computer subsystem may be zero power, full power, or some partial power of the second light beam. For example, if the scattered light due to the first light beam indicates a relatively large particle on the wafer, then the computer subsystem may determine that the second light beam should be directed to the wafer at zero or partial power to prevent the particle from disintegrating due to heating by the full power of the second light beam. Alternatively, if the scattered light due to the first light beam indicates that no relatively large particles are on the wafer, then the computer subsystem may determine that the second light beam should be directed to the wafer at full power to enable detection of relatively small particles. Such an embodiment may be further configured as described herein.

In one such embodiment, the illumination subsystem includes a Q-switched and the computer subsystem attenuates a power of the Q-switched laser based on the determined power. For example, the computer subsystem may be coupled to the Q-switched laser in any suitable manner such that the computer subsystem can control the power of the laser to match the power determined by the computer subsystem.

In one such embodiment, the computer subsystem is configured to monitor a power of the second of the multiple light beams that is actually directed to the substantially the same area to normalize the power of the second of the multiple light beams that is actually directed to the substantially the same area. In this manner, software and hardware may be used for normalization of pulse-to-pulse laser energy variations. Such an embodiment is advantageous since the pulse-to-pulse energy variation of a Q-switched laser may not be insubstantial.

Although the systems described herein may normalize the system for changes in the laser pulse energy by attenuating the power of the light beams that are directed to the substantially the same area, the systems described herein may also or alternatively normalize the system for the laser pulse energy changes by detecting the energy of the laser pulses and normalizing the gain of a sensor based on the detected energy and/or normalizing the output produced by the sensor using the computer subsystem.

In one embodiment, the system includes an optical element configured to separate the scattered light collected in different segments of a collection NA of the collection subsystem, the sensor is configured to detect one of the different segments, and the system includes another sensor configured to detect another of the different segments. In one such embodiment, the system is configured to alter or replace the optical element depending on the one of the different segments that is to be detected by the sensor and the other of the different segments that is to be detected by the other sensor. Such embodiments may be configured as further described and shown herein.

In another embodiment, the system includes an optical element configured to separate the scattered light collected in different segments of a collection NA of the collection subsystem, the sensor is configured to detect one of the different segments using one portion of the sensor and to detect another of the different segments using a different portion of the sensor, and the one portion and the other portion of the sensor do not overlap with each other and are not contiguous on the sensor. Such an embodiment may be configured as further described and shown herein.

In some embodiments, the system includes an additional sensor that includes an image intensifier, the collection subsystem is configured to image the light scattered from the substantially the same area on the wafer to the additional sensor, the additional sensor generates additional output responsive to the scattered light, and the computer subsystem is configured to detect the defects on the wafer using the additional output instead of the output when sensor electronic noise dominates total channel noise in the sensor. Such an embodiment may be configured as further described and shown herein.

In another embodiment, the system includes an additional sensor that is configured for photon counting, the collection subsystem is configured to image the light scattered from the substantially the same area on the wafer to the additional sensor, the additional sensor generates additional output responsive to the scattered light, and the computer subsystem is configured to detect the defects on the wafer using the additional output. Such an embodiment may be configured as further described herein.

In one embodiment, the system includes a MEMS-based optical switching device positioned between the collection subsystem and the sensor. In one such embodiment, the system includes at least one additional sensor, the multiple light beams include pulses of light, the scattered light includes pulses of scattered light, and the optical switching device is configured to direct a first of the pulses of scattered light generated by a first set of the pulses of light to the sensor and a second of the pulses of scattered light generated by a second set of the pulses of light, subsequent to the first set of the pulses of light, to the at least one additional sensor. In another such embodiment, the multiple light beams include pulses of light, the scattered light includes pulses of scattered light, the optical switching device is configured to separate the pulses of scattered light collected in different segments of a collection NA of the collection subsystem, and the optical switching device is configured to direct only one of the different segments of the pulses of scattered light generated by a first set of the pulses of light to the sensor and then to direct only another one of the different segments of the pulses of scattered light generated by a second set of the pulses of light, subsequent to the first set of the pulses of light, to the sensor. Such embodiments may be configured as further described and shown herein.

In one embodiment, the multiple light beams include pulses of light, the scattered light includes pulses of scattered light, the scanning subsystem is configured to scan the pulses of light across the wafer by rotating the wafer, and when the pulses of light are being scanned across a center region of the wafer, the illumination subsystem is configured to direct the pulses of light to the substantially the same area on the wafer less often than When the pulses of light are being scanned across the wafer outside of the center region. Such an embodiment may be configured as further described herein.

In another embodiment, the multiple light beams include pulses of light, the scattered light includes pulses of scattered light, the scanning subsystem is configured to scan the pulses of light across the wafer by rotating and translating the wafer, the sensor includes an area sensor, when the pulses of light are being scanned across a center region of the wafer, the scanning subsystem scans the pulses of light across the wafer in one or more non-curved lines, and when the pulses of light are being scanned across the wafer outside of the center region, the scanning subsystem scans the pulses of light across the wafer in a spiral fashion. Such an embodiment may be configured as further described herein.

Each of the embodiments of the system described above may be further configured as described herein.

An additional embodiment relates to a system configured to inspect a wafer. This system includes an illumination subsystem configured to direct a first of multiple pulsed light beams to an area on a wafer earlier in time than a second of the multiple pulsed light beams is directed to the area by the illumination subsystem. The first and second of the multiple pulsed light beams have different shapes and sizes on the wafer from each other. The first and second of the multiple pulsed light beams have different wavelengths from each other, different polarizations from each other, or different wavelengths and polarizations from each other. This illumination subsystem may be configured as described and shown further herein.

The system also includes a scanning subsystem configured to scan the multiple pulsed light beams across the wafer. This scanning subsystem may be configured in this manner as described and shown further herein. In addition, the system includes a collection subsystem configured to image light scattered from the area on the wafer to one or more sensors. The one or more sensors generate output responsive to the scattered light. The collection subsystem and the one or more sensors may be configured as described and shown further herein.

The system further includes a computer subsystem configured to detect defects on the wafer using the output of the one or more sensors and to use the output responsive to the scattered light from the area due to illumination by the first of the multiple pulsed light beams to determine a power of the second of the multiple pulsed light beams that should be directed to the area. The computer subsystem may be configured as described and shown further herein.

In one embodiment, the illumination subsystem includes a Q-switched laser, and the computer subsystem attenuates a power of the Q-switched laser based on the determined power. In another embodiment, the illumination subsystem includes a Q-switched laser, and if the determined power is zero, then the computer subsystem prevents the Q-switched laser from generating the second of the multiple pulsed light beams that would illuminate the area. In an additional embodiment, the computer subsystem is configured to monitor a power of the second of the multiple pulsed light beams that is actually directed to the area and to alter one or more parameters of the system based on the power directed to the area to normalize the power of the second of the multiple light beams that is actually directed to the area. Such embodiments may be configured as further described herein.

Each of the embodiments described above may be further configured as described herein.

A further embodiment relates to another system configured to inspect a wafer. This system includes an illumination subsystem configured to direct pulses of light to an area on a wafer. The illumination subsystem may be configured as described and shown further herein.

In one embodiment, the illumination subsystem includes a frequency conversion laser, the pulses of light directed to the area on the wafer do not vary spatially over the duration of the pulses of light and have substantially constant intensity over the duration of the pulses of light, and the pulses of light illuminate the area on the wafer in area illumination mode. In one such embodiment, the illumination subsystem includes a beam shaping optical element coupled to the laser. In another embodiment, the illumination subsystem includes a frequency conversion laser, the pulses of light directed to the area on the wafer have substantially constant intensity over the duration of the pulses of light, and the pulses of light illuminate the area on the wafer in area illumination mode. These embodiments may be configured as further described herein.

The system also includes a scanning subsystem configured to scan the pulses of light across the wafer. The scanning subsystem may be configured as described and shown further herein.

In one embodiment, the scanning subsystem is configured to scan the pulses of light across the wafer by rotating the wafer, and when the pulses of light are being scanned across a center region of the wafer, the illumination subsystem is configured to direct the pulses of light to the area on the wafer less often than when the pulses of light are being scanned across the wafer outside of the center region. Such an embodiment may be configured as further described herein.

In another embodiment, the scanning subsystem is configured to scan the pulses of light across the wafer by rotating and translating the wafer, the sensor includes an area sensor, when the pulses of light are being scanned across a center region of the wafer, the scanning subsystem scans the pulses of light across the wafer in one or more non-curved lines, and when the pulses of light are being scanned across the wafer outside of the center region, the scanning subsystem scans the pulses of light across the wafer in a spiral fashion. Such an embodiment may be configured as further described herein.

Laser repetition rates of 1 KHz and higher are generally acceptable. One obvious disadvantage of relatively high repetition rate or CW lasers on a rotating area inspection system is the undesirably high data rates required to avoid the smearing of images during a single sensor acquisition cycle. However, lower repetition rates can increase the probability of wafer damage. Some wafers (e.g., those including organic films) are more easily damaged. For the same average laser intensity incident on a wafer, a lower repetition rate will more likely damage the wafer than a higher repetition rate, if non-linear heating effects are ignored. With a relatively low repetition rate, the intensity of the laser illumination can be spread out over a larger area thereby reducing the damage probability but the optics field of view, and potentially sensor size, requirements will increase and add substantial cost to the system. The maximum laser repetition rate, with one laser pulse per frame, can also be constrained by the maximum sensor frame rate. The sensor frame rate, however, could potentially be increased by decreasing the number of active pixels or elements on the sensor.

To avoid surface damage while improving sensitivity, multiple laser pulses per area on the wafer may be used. The sample is still moved continuously but a large overlap in exposed areas exist between subsequent light source pulses. In this case, the sensor speed (frame rate) can be increased to maintain the inspection throughput. The scattering signals generated by each individual laser pulse could be read from the sensor, registered, overlaid, and processed in the post-sensor hardware or software.

Alternatively, the system includes a collection subsystem configured to image pulses of light scattered from the area on the water to a sensor. The sensor is configured to integrate a number of the pulses of scattered light that is fewer than a number of the pulses of scattered light that can be imaged on the entire area of the sensor. In this manner, the sensor may be run in partial TDI mode/partial CCD mode. For example, a sensor may be run in TDI mode to effectively optically integrate one or two (or another suitably small number of) pulses. In some embodiments, the number of pulses integrated by the sensor is one pulse of the scattered light, and the sensor integrates for the duration of the one pulse of the scattered light and then transfers any charge responsive to the one pulse of the scattered light off of the sensor. With only a small number of pulses, the "smearing" effect of a rectangular sensor operating on an r-theta inspection system can be limited. For example, the number of pixels that are integrated may be only 2 or 3 pixels, which may be achieved by limiting the number of pixels that are integrated, which is different from the manner integration is normally performed using sensors (e.g., the pixels over the whole sensor are normally integrated). The sensor is configured to generate output responsive to the integrated pulses of scattered light. The collection subsystem and the sensor may be further configured as described and shown herein. Such an embodiment may also be configured as described in U.S. Patent Application Ser. No. 61/569,611 by Chaung et al. filed Dec. 12, 2011, which is incorporated by reference as if fully set forth herein.

In one embodiment, the collection subsystem includes a scattered light collector having a resolution that is not fully diffraction-limited. Such an embodiment may he further configured as described herein.

Figure 14:
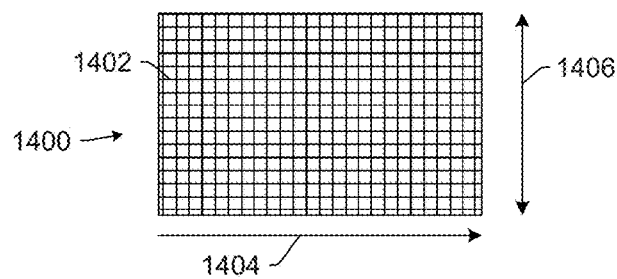
FIG. 14 is a schematic diagram illustrating a plan view of one embodiment of a sensor that includes a rectangular array of pixels.

In one embodiment, the scanning subsystem is configured to scan the pulses of light across the wafer by rotating and translating the wafer simultaneously, and the sensor includes a rectangular array of pixels. For example, as shown in FIG. 14, sensor 1400 may include a rectangular array of pixels 1402.

In another embodiment, the collection subsystem includes one or more anamorphic optical elements configured to image all of the scattered light in one of the pulses of scattered light to only one pixel of the sensor. For example, the anamorph ratio of the optics included in the collection subsystem may be changed to collect all light onto one pixel. One other way to solve the problem of the laser pulse extending across a number of pixels due to the duration of the laser pulse is to have a magnifying optic that magnifies the smeared image of the spot such that it ends up being round on the sensor instead of elliptical. One of the optical axes would have a different magnification than the other axis. Apart from the issue of finite duration laser pulses, these anamorphic optical configurations can also be used to match channels that employ optical sensors of different aspect ratios, resolutions, and/or sizes.

In an additional embodiment, the sensor integrates unidirectionally for the duration of a pulse of the scattered light and then bidirectionally transfers any charge responsive to the pulse of the scattered light off of the sensor. For example, as shown in FIG. 14, the sensor may integrate unidirectionally in one direction shown by arrow 1404 and then transfer any charge bidirectionally as shown by arrow 1406. As further shown in FIG. 14, the direction of integration may be perpendicular to the directions of charge transfer. In this manner, the sensor may integrate during the duration of the pulse, then reverse the charge transfer direction on the sensor. In addition, the sensor may be a CCD, and many CCDs allow charge to be transferred off both sides of the CCDs thereby effectively doubling the data rate. However, the laser spot only smears towards one of the sides of the sensor. Therefore, if you integrate unidirectionally, then stop once the laser pulse is complete, and then shift charge off bidirectionally, you get most of the data rate/throughput advantage while still optically integrating all the light.

In some embodiments, the sensor includes an image intensifier and an area sensor, and the sensor integrates for the duration of a pulse of the scattered light and until all phosphor energy of the image intensifier corresponding to the pulse of the scattered light has completely decayed. In such embodiments, the sensor may be a TDI sensor, a CCD or a CMOS sensor. For example, if a sensor is detecting the output of an image intensifier, the image intensifier includes a phosphor (like a TV) that takes a relatively long time to decay. One can integrate the pixels of a sensor for as long as necessary to collect all this phosphor energy, then start transferring charge (in the case of a CCD) or reading out the pixel voltage (in the case of a CMOS). Obviously, this will cost the throughput of waiting for the phosphor to decay, but at least all the energy will be collected in a small number of pixels. Such an embodiment may be further configured as described and shown herein.

In one embodiment, the sensor is synchronized in time relative to the pulses of light to detect only the pulses of scattered light with predetermined arrival times. In one such embodiment, the pulses of the scattered light with the predetermined arrival times include fluorescence or photoluminescence. Such embodiments may be further configured as described and shown herein.

The system further includes a computer subsystem configured to detect defects on the wafer using the output generated by the sensor. The computer subsystem may be further configured as described and shown herein.

In one embodiment, the system includes an optical element configured to separate the pulses of the scattered light collected in different segments of a collection NA of the collection subsystem, the sensor is configured to detect one of the different segments, and the system includes another sensor configured to detect another of the different segments. In one such embodiment, the system is configured to alter or replace the optical element depending on the one of the different segments that is to be detected by the sensor and the other of the different segments that is to be detected by the other sensor. Such embodiments may be further configured as described and shown herein.

In one embodiment, the system includes an optical element configured to separate the pulses of the scattered light collected in different segments of a collection NA of the collection subsystem, the sensor is configured to detect one of the different segments using one portion of the sensor and to detect another of the different segments using a different portion of the sensor, and the one portion and the other portion of the sensor do not overlap with each other and are not contiguous on the sensor. Such an embodiment may be further configured as described and shown herein.

In some embodiments, the system includes an additional sensor that includes an image intensifier, the collection subsystem is configured to image the pulses of light scattered from the area on the wafer to the additional sensor, the additional sensor generates additional output responsive to the pulses of scattered light, and the computer subsystem is configured to detect the defects on the wafer using the additional output instead of the output when sensor electronic noise dominates total channel noise in the sensor. Such an embodiment may be further configured as described and shown herein.

In an embodiment, the system includes an additional sensor that is configured for photon counting, the collection subsystem is configured to image the pulses of light scattered from the area on the wafer to the additional sensor, the additional sensor generates additional output responsive to the pulses of scattered light, and the computer subsystem is configured to detect the defects on the wafer using the additional output. Such an embodiment may be further configured as described and shown herein.

In some embodiments, the system includes a MEMS-based optical switching device positioned between the collection subsystem and the sensor. In one such embodiment, the system includes at least one additional sensor, the optical switching device is configured to direct a first of the pulses of scattered light generated by a first of the pulses of light to the sensor and a second of the pulses of scattered light generated by a second of the pulses of light, subsequent to the first of the pulses of light, to the at least one additional sensor. In another such embodiment, the optical switching device is configured to separate the pulses of scattered light collected in different segments of a collection NA of the collection subsystem, and the optical switching device is configured to direct only one of the different segments of the scattered light generated by a first of the pulses of light to the sensor and then to direct only another one of the different segments of the scattered light generated by a second of the pulses of light, subsequent to the first of the pulses of light, to the sensor. Such embodiments may be configured as further described and shown herein.

Each of the embodiment described above may be further configured as described herein.

Another embodiment relates to a system configured to inspect a wafer. This system includes an illumination subsystem configured to direct light to an area on a wafer. This illumination subsystem may be configured as described and shown further herein. The system also includes a scanning subsystem configured to scan the light across the wafer. This scanning subsystem may be configured as described and shown further herein. In addition, the system includes a collection subsystem configured to image light scattered from the area on the wafer to a sensor. The sensor is configured to generate output responsive to the scattered light. The collection subsystem and the sensor may be configured as described and shown further herein.

Figure 15:
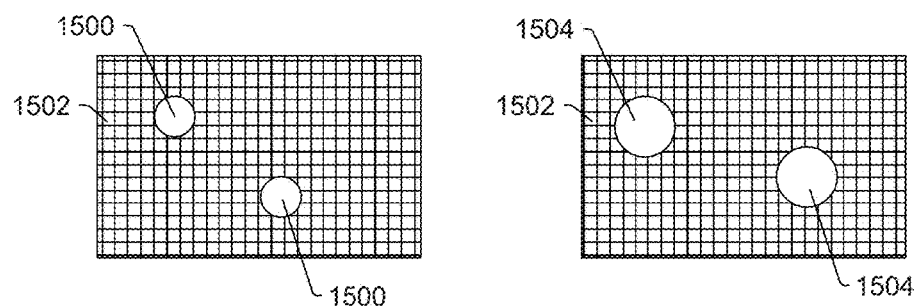
FIG. 15 is a schematic diagram illustrating a plan view of how sizes, in pixels, of point defects can vary depending on a focal condition of a system configured to inspect a wafer.

The system further includes a computer subsystem configured to detect point defects on the wafer using the output generated by the sensor, to determine a size, in pixels, of the point defects, to determine a focal condition of the system based on the size of the point defects, and to alter one or more parameters of the system based on the focal condition. In this manner, the system may perform autofocus by looking at the point spread function of defects. In other words, one potential means of determining the height of the wafer is to look at the size of point defects, in pixels, being detected by the actual inspection process. As such, the embodiments described herein may be configured for measuring focus conditions with an inspection algorithm. In particular, since many defects detected on an unpatterned inspection system will be point defects on top of a substantially small background, the algorithm that detects these defects, imaged onto a 2D sensor, can also characterize the size of these defects. If the defects are larger than that specified by the system calibration, this can correspond to a defocus condition. For example, as shown in FIG. 15, defects 1500 imaged onto two-dimensional sensor 1502 will have one size when the system is in focus, and defects 1504 imaged onto the same two-dimensional sensor 1502 will have a different (e.g., larger) size When the system is out of focus. Such embodiments can render a separate autofocus sensing system unnecessary or an existing autofocus sensing system can be made simpler.

The one or more parameters of the system that are altered by the computer subsystem may include position of the inspection illumination, position of illumination optics, collection optics, wafer height, tilt of wafer, tilt of chuck, or temperature and/or pressure within the inspection system. The one or more parameters may be altered using a feed forward technique. The depth of focus of the system can depend on the apertures and/or polarizers present in the collection optics between the wafer and the sensor(s) as mentioned above, and the system operation can be configured to account for these various inspection modes developed to optimize the inspection of different types of wafers.

Determining the height of the wafer based on the size of point defects is most advantageously done in an unpatterned inspection application. In a patterned wafer inspection application, there are many different structures on the wafer that scatter light onto the sensor. Each of these structures may be of a size smaller or larger than the imaging lens point spread function. It would be difficult to ascertain which scattered light pattern(s) in any particular sensor frame would provide the proper autofocus error signal. On the other hand, in an unpatterned inspection application, many defects are point defects, and are sized substantially smaller than the imaging system point spread function (which may be approximately 250 to 300 nm), and therefore, all will appear on the sensor to be nearly the exact size of the point spread function. In this case, deviations can be easily calculated.

In one embodiment, the computer subsystem is configured to determine the focal condition and alter the one or more parameters during an inspection process performed on the wafer. In this manner, the computer subsystem can control the focus in situ and thereby keep the wafer in focus during the inspection process. The computer subsystem can be configured in any suitable manner to perform in situ control.

In another embodiment, the system includes an additional subsystem configured to direct other light to an additional area on the wafer in advance of the light being directed to the area by the illumination subsystem, the additional subsystem includes an additional sensor configured to detect light scattered from the additional area, and the computer subsystem is configured to alter a power of the light being directed to the area by the illumination subsystem based on the detected light scattered from the additional area. The area and the additional area may be configured as shown in FIG. 11 except in this embodiment the area and the additional area do not necessarily have different sizes and shapes. In addition, the additional subsystem may be arranged in a manner similar to that shown in FIG. 12 in which one of light sources 1200, 1202, and 1204 is used as the light source for the additional subsystem and one of sensors 130 and 502 is used as the sensor of the additional subsystem. In this manner, the additional subsystem and the main inspection subsystem may both utilize some of the same optical elements such as refractive optical element 912 and scattered light collector 122. The additional subsystem may include any other suitable optical elements. The computer subsystem may be configured in this embodiment as described further herein to alter the power of the light being directed to the area by the illumination subsystem.

In some embodiments, the collection subsystem is configured to image the light scattered from the area on the wafer to one or more additional sensors, the one or more additional sensors are configured to generate output responsive to the scattered light, each of the sensor and the one or more additional sensors are configured to detect the scattered light collected in different segments of a collection NA of the collection subsystem, and the computer subsystem is configured to detect the point defects on the wafer using the output generated by the one or more additional sensors, to determine different sizes, in pixels, for at least one of the point defects using different output, respectively, generated for the at least one of the point defects by the one or more additional sensors, to determine a weighted size for the at least one of the point defects based on the size and the different sizes, to determine the focal condition of the system based on the weighted size, and to alter the one or more parameters of the system based on the focal condition. For example, the point spread functions may be weighted by the various channels (each channel generates a slightly different point spread function, because each channel collects a different portion of the scattering hemisphere) to get a better feedback signal. This collection subsystem, additional sensor(s), and computer subsystem may be further configured as described herein.

In another embodiment, the collection subsystem is configured to image the light scattered from different point defects on the wafer onto different portions of the sensor, and the computer subsystem is configured to determine if and how the wafer is tilted based on a relationship between the sizes of the different point defects and the different portions of the sensor on which the light scattered from the different point defects was imaged. For example, tilt of the wafer may be corrected in real time by tilting the gripping chuck, based on the response across the sensor (e.g., a point spread function for one defect at an edge of the sensor versus a point spread function for another defect at the middle of the sensor may indicate that the wafer is not level and therefore that the wafer should be tilted).

Each of the embodiments described above may be further configured as described herein.

An additional embodiment relates to a system configured to inspect a wafer. The system includes an illumination subsystem configured to direct light to an area on a wafer. The light illuminates the area on the wafer in area illumination mode. This illumination subsystem may be configured as described and shown further herein.

In one embodiment, the illumination subsystem includes a frequency conversion laser, the light includes pulses of light, and the pulses of light directed to the area on the wafer do not vary spatially over the duration of the pulses of light and have substantially constant intensity over the duration of the pulses of light. In one such embodiment, the illumination subsystem includes a beam shaping optical element coupled to the laser. Such embodiments may be further configured as described and shown herein. In some embodiments, the illumination subsystem includes a frequency conversion laser, the light includes pulses of light, and the pulses of light directed to the area on the wafer have substantially constant intensity over the duration of the pulses of light. Such an embodiment may be configured as described further herein.

The system also includes a scanning subsystem configured to scan the light across the wafer. This scanning subsystem may be configured as further described and shown herein.

In one embodiment, the light includes pulses of light, the scattered light includes pulses of scattered light, the scanning subsystem is configured to scan the pulses of light across the wafer by rotating the wafer, and when the pulses of light are being scanned across a center region of the wafer, the illumination subsystem is configured to direct the pulses of light to the area on the wafer less often than when the pulses of light are being scanned across the wafer outside of the center region. In another embodiment, the light includes pulses of light, the scattered light includes pulses of scattered light, the scanning subsystem is configured to scan the pulses of light across the wafer by rotating and translating the wafer, the sensor includes an area sensor, when the pulses of light are being scanned across a center region of the wafer, the scanning subsystem scans the pulses of light across the wafer in one or more non-curved lines, and when the pulses of light are being scanned across the wafer outside of the center region, the scanning subsystem scans the pulses of light across the wafer in a spiral fashion. Such embodiments may be further configured as described herein.

In addition, the system includes a collection subsystem configured to image light scattered from the area on the wafer to a sensor. The sensor is configured to generate output responsive to the scattered light. This collection subsystem and sensor may be configured as further described and shown herein.

In one embodiment, the light includes pulses of light, the scattered light includes pulses of scattered light, and the sensor is synchronized in time relative to the pulses of light to detect only the pulses of scattered light with predetermined arrival times. In one such embodiment, the pulses of the scattered light with the predetermined arrival times include fluorescence or photoluminescence. Such embodiments may be further configured as described herein.

The system also includes a computer subsystem configured to detect defects on the wafer using the output generated by the sensor. The computer subsystem may be configured as further described and shown herein.

In one embodiment, the system includes an additional sensor that includes an image intensifier, the collection subsystem is configured to image the light scattered from the area on the wafer to the additional sensor, the additional sensor generates additional output responsive to the scattered light, and the computer subsystem is configured to detect the defects on the wafer using the additional output instead of the output when sensor electronic noise dominates total channel noise in the sensor. Such an embodiment may be further configured as described and shown herein.

In another embodiment, the system includes an additional sensor that is configured for photon counting, the collection subsystem is configured to image the light scattered from the area on the wafer to the additional sensor, the additional sensor generates additional output responsive to the scattered light, and the computer subsystem is configured to detect the defects on the wafer using the additional output. Such an embodiment may be further configured as described herein.

In some embodiments, the system includes a MEMS-based optical switching device positioned between the collection subsystem and the sensor. In one such embodiment, the system includes at least one additional sensor, the light includes pulses of light, the scattered light includes pulses of scattered light, and the optical switching device is configured to direct a first of the pulses of scattered light generated by a first of the pulses of light to the sensor and a second of the pulses of scattered light generated by a second of the pulses of light, subsequent to the first of the pulses of light, to the at least one additional sensor. In another such embodiment, the includes pulses of light, the scattered light includes pulses of scattered light, the optical switching device is configured to separate the pulses of scattered light collected in different segments of a collection NA of the collection subsystem, and the optical switching device is configured to direct only one of the different segments of the pulses of scattered light generated by a first of the pulses of light to the sensor and then to direct only another one of the different segments of the pulses of scattered light generated by a second of the pulses of light, subsequent to the first of the pulses of light, to the sensor. Such embodiments may be further configured as described and shown herein.

Each of the embodiments described above may be further configured as described herein.

Any of the systems described herein may include additional channels and/or subsystems (not shown) designed to detect defects independently or in conjunction with the main inspection optical channels described above. One example of such an additional channel is a Nomarski differential interference contrast (DIC) "bright field" channel.

All channels of any of the inspection systems described herein generate information regarding the surface quality as well as defects of interest. The output from multiple channels may be combined by various logical means and/or with various mathematic operations as described in U.S. Patent Application Publication Nos. 2010/0188657 published on Jul. 29, 2010 to Chen et al. and 2012/0044486 published on Feb. 23, 2012 to Chen et al., which are incorporated by reference as if fully set forth herein. Sometimes this is referred to as image or channel fusion and can advantageously improve anomaly capture rate while decreasing the false count rate.

The embodiments described herein may also be further configured as described in U.S. Pat. No. 7,286,697 to Guetta, U.S. Pat. No. 7,339,661 to Korngut et al., U.S. Pat. No. 7,525,659 to Furman et al., U.S. Pat. No. 7,826,049 to Furman et al., and U.S. Pat. No. 7,843,558 to Furman, all of which are incorporated by reference as if fully set forth herein.

Further modifications and alternative embodiments of various aspects of the invention may be apparent to those skilled in the art in view of this description. For example, systems configured to inspect a wafer are provided. Accordingly, this s description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a wafer, comprising:
an illumination subsystem configured to direct multiple light beams to substantially the same area on a wafer, wherein the multiple light beams have substantially the same wavelength and polarization characteristics;
a scanning subsystem configured to scan the multiple light beams across the wafer;
a collection subsystem configured to image light scattered from the substantially the same area on the wafer to a sensor, wherein the sensor generates output responsive to the scattered light; and
a computer subsystem configured to detect defects on the wafer using the output of the sensor, wherein the computer subsystem is further configured to use the output responsive to the scattered light from the substantially the same area due to illumination by a first of the multiple light beams to determine a power of a second of the multiple light beams that should be directed to the substantially the same area.

2. The system of claim 1, wherein the multiple light beams arc directed to the substantially the same area on the wafer at substantially the same polar angles and different azimuth angles.

3. The system of claim 1, wherein the multiple light beams are directed to the substantially the same area on the wafer simultaneously.

4. The system of claim 1, wherein the multiple light beams are laser beams.

5. The system of claim 1, wherein the multiple light beams illuminate the substantially the same area on the wafer in area illumination mode.

6. The system of claim 1, wherein the substantially the same area on the wafer has a lateral dimension of greater than 50 microns.

7. The system of claim 1, wherein the multiple light beams are pulsed light beams, and wherein the illumination subsystem is further configured to direct the second of the multiple light beams to the substantially the same area on the wafer later than the first of the multiple light beams is directed to the substantially the same area by the illumination subsystem such that a peak pulse power incident on the wafer due to the multiple light beams is less than if the multiple light beams were directed to the substantially the same area on the wafer at the same time.

8. The system of claim 1, wherein the multiple light beams are pulsed light beams, and wherein the illumination subsystem is further configured to direct the second of the multiple light beams to the substantially the same area on the wafer later than the first of the multiple light beams is directed to the substantially the same area by the illumination subsystem such that the pulsed light beams illuminate the substantially the same area as one continuous pulse of light having a duration longer than each of the pulsed light beams.

9. The system of claim 1, wherein the multiple light beams are pulsed light beams, wherein the illumination subsystem is further configured to direct the first of the multiple light beams to the substantially the same area on the wafer earlier in time than the second of the multiple fight beams is directed to the substantially the same area by the illumination subsystem, wherein the first and second of the multiple light beams have different shapes and sizes on the wafer from each other, and wherein the computer subsystem is further configured to use the output responsive to the scattered light from the substantially the same area due to illumination by the first of the multiple light beams to determine if the second of the multiple light beams should be directed to the substantially the same area.

10. The system of claim 9, wherein the illumination subsystem comprises a Q-switched laser, and Wherein if the computer subsystem determines that the second of the multiple light beams should not be directed to the substantially the same area, then the computer subsystem prevents the second of the multiple light beams from illuminating the substantially the same area.

11. The system of claim 1, wherein the multiple light beams are pulsed light beams, wherein the illumination subsystem is further configured to direct the first of the multiple light beams to the substantially the same area on the wafer earlier in time than the second of the multiple fight beams is directed to the substantially the same area by the illumination subsystem, and wherein the first and second of the multiple light beams have different shapes and sizes on the wafer from each other.

12. The system of claim 11, wherein the illumination subsystem comprises a Q-switched laser, and wherein the computer subsystem attenuates a power of the Q-switched laser based on the determined power.

13. The system of claim 11, wherein the computer subsystem is further configured to monitor a power of the second of the multiple light beams that is actually directed to the substantially the same area and to alter one or more parameters of the system based on the power directed to the substantially the same area to normalize the power of the second of the multiple light beams that is actually directed to the substantially the same area.

14. The system of claim 1, wherein the multiple light beams are generated by only one single laser of the illumination subsystem.

15. The system of claim 1, wherein the multiple light beams are generated by multiple lasers of the illumination subsystem.

16. The system of claim 1, wherein the multiple light beams comprise one light beam generated by a light source of the illumination subsystem and another light beam formed by collecting light reflected from the substantially the same area on the wafer and directing the collected reflected light back to the substantially the same area on the wafer.

17. The system of claim 1, wherein the illumination subsystem is further configured to vary the multiple light beams directed to the substantially the same area on the wafer as a function of time, wherein the collection subsystem is further configured to image the light scattered from multiple areas on the wafer to the sensor, and wherein the sensor and a light source of the illumination subsystem are gated in sync with one another.

18. The system of claim 17, wherein the multiple light beams are directed to the substantially the same area on the wafer at different azimuth angles, different polar angles, or different azimuth and polar angles.

19. The system of claim 17, wherein the illumination subsystem is further configured to alter the wavelength and polarization characteristics of the multiple light beams, and wherein the multiple light beams directed to the substantially the same area on the wafer as the function of time have different wavelength characteristics from each other, different polarization characteristics from each other, or different wavelength and polarization characteristics from each other.

20. The system of claim 1, further comprising an optical element configured to separate the scattered light collected in different segments of a collection numerical aperture of the collection subsystem, wherein the sensor is further configured to detect one of the different segments, and wherein the system further comprises another sensor configured to detect another of the different segments.

21. The system of claim 20, wherein the system is further configured to alter or replace the optical element depending on the one of the different segments that is to be detected by the sensor and the other of the different segments that is to he detected by the other sensor.

22. The system of claim 1, further comprising an optical element configured to separate the scattered light collected in different segments of a collection numerical aperture of the collection subsystem, wherein the sensor is further configured to detect one of the different segments using one portion of the sensor and to detect another of the different segments using a different portion of the sensor, and wherein the one portion and the other portion of the sensor do not overlap with each other and are not contiguous on the sensor.

23. The system of claim 1, wherein the collection subsystem comprises a scattered light collector having a resolution that is not fully diffraction-limited.

24. The system of claim 1, further comprising an additional sensor that includes an image intensifier, wherein the collection subsystem is further configured to image the light scattered from the substantially the same area on the wafer to the additional sensor, wherein the additional sensor generates additional output responsive to the scattered light, and wherein the computer subsystem is further configured to detect the defects on the wafer using the additional output instead of the output when sensor electronic noise dominates total channel noise in the sensor.

25. The system of claim 1, further comprising an additional sensor that is configured for photon counting, wherein the collection subsystem is further configured to image the light scattered from the substantially the same area on the wafer to the additional sensor, wherein the additional sensor generates additional output responsive to the scattered light, and wherein the computer subsystem is further configured to detect the defects on the wafer using the additional output.

26. The system of claim 1, wherein the illumination subsystem comprises a frequency conversion laser, wherein the multiple light beams comprise pulses of light, and wherein the pulses of light directed to the substantially the same area on the wafer do not vary spatially over the duration of the pulses of light and have substantially constant intensity over the duration of the pulses of light.

27. The system of claim 26, wherein the illumination subsystem further comprises a beam shaping optical element coupled to the laser.

28. The system of claim 1, wherein the illumination subsystem comprises a frequency conversion laser, wherein the multiple light beams comprise pulses of light, and wherein the pulses of light directed to the substantially the same area on the wafer have substantially constant intensity over the duration of the pulses of light.

29. The system of claim 1, further comprising a micro-electro-mechanical system-based optical switching device positioned between the collection subsystem and the sensor.

30. The system of claim 29, further comprising at least one additional sensor, wherein the multiple light beams comprise pulses of light, wherein the scattered light comprises pulses of scattered light, and wherein the optical switching device is configured to direct a first of the pulses of scattered light generated by a first set of the pulses of light to the sensor and a second of the pulses of scattered light generated by a second set of the pulses of light, subsequent to the first set of the pulses of light, to the at least one additional sensor.

31. The system of claim 29, wherein the multiple light beams comprise pulses of light, wherein the scattered light comprises pulses of scattered light, wherein the optical switching device is configured to separate the pulses of scattered light collected in different segments of a collection numerical aperture of the collection subsystem, and wherein the optical switching device is further configured to direct only one of the different segments of the pulses of scattered light generated by a first set of the pulses of light to the sensor and then to direct only another one of the different segments of the pulses of scattered light generated by a second set of the pulses of light, subsequent to the first set of the pulses of light, to the sensor.

32. The system of claim 1, Wherein the multiple light beams comprise pulses of light, wherein the scattered light comprises pulses of scattered light, and wherein the sensor is synchronized in time relative to the pulses of light to detect only the pulses of scattered light with predetermined arrival times.

33. The system of claim 32, wherein the pulses of scattered light with the predetermined arrival times comprise fluorescence or photoluminescence.

34. The system of claim 1, wherein the multiple light beams comprise pulses of light, wherein the scattered light comprises pulses of scattered light, wherein the scanning subsystem is further configured to scan the pulses of light across the wafer by rotating the wafer, and wherein when the pulses of light are being scanned across a center region of the wafer, the illumination subsystem is further configured to direct the pulses of light to the substantially the same area on the wafer less often than When the pulses of light are being scanned across the wafer outside of the center region.

35. The system of claim 1, wherein the multiple light beams comprise pulses of light, wherein the scattered light comprises pulses of scattered light, wherein the scanning subsystem is further configured to scan the pulses of light across the wafer by rotating and translating the wafer, wherein the sensor comprises an area sensor, wherein when the pulses of light are being scanned across a center region of the wafer, the scanning subsystem scans the pulses of light across the wafer in one or more non-curved lines, and wherein when the pulses of light are being scanned across the wafer outside of the center region, the scanning subsystem scans the pulses of light across the wafer in a spiral fashion.

36. A system configured to inspect a wafer, comprising:
an illumination subsystem configured to direct a first of multiple pulsed light beams to an area on a wafer earlier in time than a second of the multiple pulsed light beams is directed to the area by the illumination subsystem, wherein the first and second of the multiple pulsed light beams have different shapes and sizes on the wafer from each other, and wherein the first and second of the multiple pulsed light beams have different wavelengths from each other, different polarizations from each other, or different wavelengths and polarizations from each other;
a scanning subsystem configured to scan the multiple pulsed light beams across the wafer;
a collection subsystem configured to image light scattered from the area on the wafer to one or more sensors, wherein the one or more sensors generate output responsive to the scattered light; and
a computer subsystem configured to detect defects on the wafer using the output of the one or more sensors and to use the output responsive to the scattered light from the area due to illumination by the first of the multiple pulsed light beams to determine a power of the second of the multiple pulsed light beams that should be directed to the area.

37. The system of claim 36, wherein the illumination subsystem comprises a Q-switched laser, and wherein the computer subsystem attenuates a power of the Q-switched laser based on the determined power.

38. The system of claim 36, wherein the illumination subsystem comprises a Q-switched laser, and wherein if the determined power is zero, then the computer subsystem prevents the Q-switched laser from generating the second of the multiple pulsed light beams that would illuminate the area.

39. The system of claim 36, wherein the computer subsystem is further configured to monitor a power of the second of the multiple pulsed light beams that is actually directed to the area and to alter one or more parameters of the system based on the power directed to the area to normalize the power of the second of the multiple light beams that is actually directed to the area.

40. A system configured to inspect a wafer, comprising:
an illumination subsystem configured to direct light to an area on a wafer;
a scanning subsystem configured to scan the light across the wafer;
a collection subsystem configured to image light scattered from the area on the wafer to a sensor, wherein the sensor is configured to generate output responsive to the scattered light; and
a computer subsystem configured to detect point defects on the wafer using the output generated by the sensor, to determine a size, in pixels, of the point defects, to determine a focal condition of the system based on the size of the point defects, and to alter one or more parameters of the system based on the focal condition.

41. The system of claim 40, wherein the computer subsystem is further configured to determine the focal condition and alter the one or more parameters during an inspection process performed on the wafer.

42. The system of claim 40, further comprising an additional subsystem configured to direct other light to an additional area on the wafer in advance of the light being directed to the area by the illumination subsystem, wherein the additional subsystem comprises an additional sensor configured to detect light scattered from the additional area, and wherein the computer subsystem is further configured to alter a power of the light being directed to the area by the illumination subsystem based on the detected light scattered from the additional area.

43. The system of claim 40, wherein the collection subsystem is further configured to image the light scattered from the area on the wafer to one or more additional sensors, wherein the one or more additional sensors are configured to generate output responsive to the scattered light, wherein each of the sensor and the one or more additional sensors are configured to detect the scattered light collected in different segments of a collection numerical aperture of the collection subsystem, and wherein the computer subsystem is further configured to detect the point defects on the wafer using the output generated by the one or more additional sensors, to determine different sizes, in pixels, for at least one of the point, defects using different output, respectively, generated for the at least one of the point defects by the one or more additional sensors, to determine a weighted size for the at least one of the point defects based on the size and the different sizes, to determine the focal condition of the system based on the weighted size, and to alter the one or more parameters of the system based on the focal condition.

44. The system of claim 40, wherein the collection subsystem is further configured to image the light scattered from different point defects on the wafer onto different portions of the sensor, and wherein the computer subsystem is further configured to determine if and how the wafer is tilted based on a relationship between the sizes of the different point defects and the different portions of the sensor on which the light scattered from the different point defects was imaged.

45. A system configured to inspect a wafer, comprising:
an illumination subsystem configured to direct multiple light beams to substantially the same area on a wafer;
a scanning subsystem configured to scan the multiple light beams across the wafer;
a collection subsystem configured to image light scattered from the substantially the same area on the wafer to a sensor, wherein the sensor is configured to generate output responsive to the scattered light; and
a computer subsystem configured to detect defects on the wafer using the output generated by the sensor, wherein the computer subsystem is further configured to use the output responsive to the scattered light from the substantially the same area due to illumination by a first of the multiple light beams to determine a power of a second of the multiple light beams that should be directed to the substantially the same area.

46. The system of claim 45, further comprising an additional sensor that includes an image intensifier, wherein the collection subsystem is further configured to image the light scattered from the substantially the same area on the wafer to the additional sensor, wherein the additional sensor generates additional output responsive to the scattered light, and wherein the computer subsystem is further configured to detect the defects on the wafer using the additional output instead of the output when sensor electronic noise dominates total channel noise in the sensor.

47. The system of claim 45, further comprising an additional sensor that is configured for photon counting, wherein the collection subsystem is further configured to image the light scattered from the substantially the same area on the wafer to the additional sensor, wherein the additional sensor generates additional output responsive to the scattered light, and wherein the computer subsystem is further configured to detect the defects on the wafer using the additional output.

48. The system of claim 45, wherein the illumination subsystem comprises a frequency conversion laser, wherein the light comprises pulses of light, and wherein the pulses of light directed to the area on the wafer do not spatially over the duration of the pulses of light and have substantially constant intensity over the duration of the pulses of light.

49. The system of claim 48, wherein the illumination subsystem further comprises a beam shaping optical element coupled to the laser.

50. The system of claim 45, wherein the illumination subsystem comprises a frequency conversion laser, wherein the light comprises pulses of light, and wherein the pulses of light directed to the area on the wafer have substantially constant intensity over the duration of the pulses of light.

51. The system of claim 45, further comprising a micro-electro-mechanical system-based optical switching device positioned between the collection subsystem and the sensor.

52. The system of claim 51, further comprising at least one additional sensor, wherein the light comprises pulses of light, wherein the scattered light comprises pulses of scattered light, and wherein the optical switching device is configured to direct a first of the pulses of scattered light generated by a first of the pulses of light to the sensor and a second of the pulses of scattered light generated by a second of the pulses of light, subsequent to the first of the pulses of light, to the at least one additional sensor.

53. The system of claim 51, wherein the light comprises pulses of light, wherein the scattered light comprises pulses of scattered light, wherein the optical switching device is configured to separate the pulses of scattered light collected in different segments of a collection numerical aperture of the collection subsystem, and wherein the optical switching device is further configured to direct only one of the different segments of the pulses of scattered light generated by a first of the pulses of light to the sensor and then to direct only another one of the different segments of the pulses of scattered light generated by a second of the pulses of light, subsequent, to the first of the pulses of light, to the sensor.

54. The system of claim 45, wherein the light comprises pulses of light, wherein the scattered light comprises pulses of scattered light, and wherein the sensor is synchronized in time relative to the pulses of light to detect only the pulses of scattered light with predetermined arrival times.

55. The system of claim 54, wherein the pulses of the scattered light with the predetermined arrival times comprise fluorescence or photoluminescence.

56. The system of claim 45, wherein the light comprises pulses of light, wherein the scattered light comprises pulses of scattered light, wherein the scanning subsystem is further configured to scan the pulses of light across the wafer by rotating the wafer, and wherein when the pulses of light are being scanned across a center region of the wafer, the illumination subsystem is further configured to direct the pulses of light to the area on the wafer less often than When the pulses of light are being scanned across the wafer outside of the center region.

57. The system of claim 45, wherein the light comprises pulses of light, wherein the scattered light comprises pulses of scattered light, wherein the scanning subsystem is further configured to scan the pulses of light across the wafer by rotating and translating the wafer, wherein the sensor comprises an area sensor, wherein when the pulses of light are being scanned across a center region of the wafer, the scanning subsystem scans the pulses of light across the wafer in one or more non-curved lines, and wherein when the pulses of light are being scanned across the wafer outside of the center region, the scanning subsystem scans the pulses of light across the wafer in a spiral fashion.

* * * * *